United States Patent [19]

Preuss et al.

[11] Patent Number: 5,595,992
[45] Date of Patent: Jan. 21, 1997

[54] SUBSTITUTED PYRIDINES AND PYRIMIDINES, PROCESSES FOR THEIR PREPARATION AND THEIR USE AS PESTICIDES AND FUNGICIDES

[75] Inventors: Rainer Preuss, Hofheim; Wolfgang Schaper, Diedorf; Martin Märkl; Harald Jakobi, both of Frankfurt; Peter Braun, Nieder-Olm; Werner Knauf, Eppstein; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Germany

[21] Appl. No.: 304,390

[22] Filed: Sep. 12, 1994

[30]   Foreign Application Priority Data

Sep. 14, 1993 [DE] Germany ............................ 43 31 178.4

[51] Int. Cl.$^6$ ................. C07D 403/12; C07D 239/32; C07D 239/46; C07D 239/70; C07D 239/72; A61K 31/505; A61K 31/52; A61K 31/50
[52] U.S. Cl. ..................... 514/254; 514/211; 514/212; 514/215; 514/221; 514/247; 514/249; 514/252; 514/255; 514/256; 514/258; 514/259; 514/261; 514/269; 540/600; 540/601; 540/476; 540/473; 544/229; 544/319; 544/326; 544/327; 544/328; 544/329; 544/284; 544/278; 544/279; 544/280; 544/255; 544/256; 544/257; 544/262; 544/264; 544/295; 544/296; 544/238; 544/236; 544/237
[58] Field of Search ..................... 544/287, 288, 544/289, 293, 319, 326, 327, 328, 329, 229, 284, 278, 255, 262, 296, 237; 540/600, 473; 514/211, 221, 252, 256, 261

[56]   References Cited

FOREIGN PATENT DOCUMENTS 0326328   8/1989   European Pat. Off. .
0414368   2/1991   European Pat. Off. .
0424125   4/1991   European Pat. Off. .
0453137  10/1991   European Pat. Off. .
0452002  10/1991   European Pat. Off. .
0467760   1/1992   European Pat. Off. .
WO93/19050  9/1993   WIPO .

OTHER PUBLICATIONS

Bergmann et al, Chemical Abstracts, vol. 79, entry 77808 (1973).

*Primary Examiner*—John M. Ford
*Attorney, Agent, or Firm*—Curtis, Morris & Safford, P.C.

[57]   ABSTRACT

Substituted pyridines and pyrimidines, processes for their preparation and their use as pesticides and fungicides.

The invention relates to compounds of the formula in which A is N or CH, R is H, halogen, alkyl or cycloalkyl, $R^2$ and $R^3$ are H, halogen or an aliphatic radical or together form a ring, X is O, NH Or $S(O)_q$ where q=0, 1 or 2, $R^4_q$ is 0–4 radicals selected from the series consisting of halogen, optionally substituted alkyl or alkoxy, cycloalkyl and optionally substituted phenyl, n=0–2, m=1–3 and Y is optionally substituted methylene or imino.

The invention furthermore relates to a process for their preparation and for their use as pesticides, in particular as insecticides, acaricides and fungicides. The compounds are furthermore suitable for controlling nematodes, helminths and molluscs, and for controlling endoparasites and ectoparasites in the field of veterinary medicine.

8 Claims, No Drawings

SUBSTITUTED PYRIDINES AND PYRIMIDINES, PROCESSES FOR THEIR PREPARATION AND THEIR USE AS PESTICIDES AND FUNGICIDES

The invention relates to novel substituted pyridines and pyrimidines and to fused systems derived therefrom, to processes for their preparation, and to their use as pesticides, in particular as insecticides, acaricides and fungicides. The compounds are furthermore suitable for controlling nematodes, helminths and molluscs, and for controlling endoparasites and ectoparasites in the field of veterinary medicine.

It has already been disclosed that certain 4-alkoxy- and 4-aminopyrimidines show a good fungicidal, acaricidal and insecticidal activity (cf. EP-A-326 328, EP-A-414 368, EP-A-424 125, EP-A-453 137 and EP-A-467 760). However, the biological activity of these compounds is not satisfactory in all areas of application, in particular at low application rates and concentrations.

Novel substituted pyridines and pyrimidines and fused systems derived therefrom have been found, which have the formula I

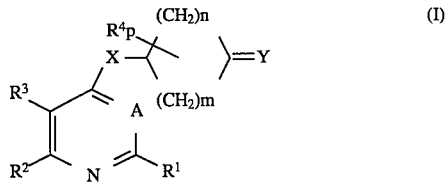

in which the radicals and variables are as defined below.

The invention therefore relates to compounds of the formula I and to acid addition salts thereof in which A is N or $R^1$ is hydrogen, halogen, $(C_1-C_4)$-alkyl or $(C_3-C_6)$-cycloalky $R^2$ is hydrogen, halogen, $(C_1-C_4)$-alkyl or $(C_1-C_4)$-haloalkyl, $(C_1-C_4)$-alkoxy, $(C_1-C_4)$-haloalkoxy,-$(C_1-C_4)$-alkoxy-$(C-C_4)$-alkyl, $(C_1-C_4)$-haloalkoxy-$(C_1-C_4)$-haloalkyl, $(C_1-C_4)$-alkylthio, $(C_1-C_4)$-alkylthio-$(C_1-C_4)$-alkyl, $(C_1-C_4)$-alkylamino or di-$(C_1-C_4)$-alkylamino, $R^3$ is hydrogen, halogen, $(C_1-C_4)$-alkyl or $(C_1-C_4)$-haloalkyl, $(C_1-C_4)$-alkoxy, $(C_1-C_4)$-haloalkoxy, $(C_1-C_4)$-alkylthio, amino, $(C_1-C_4)$-alkylamino or di-$(C_1-C_4)$-alkylamino, or $R^2$ and $R_3$ together with the carbon atoms to which they are bonded form an unsaturated 5- or 6-membered isocyclic ring which can also contain one or more, preferably one or two, nitrogen atoms and which, in the event that it is a 5-membered ring, can contain an oxygen or sulfur atom instead of $CH_2$ and which is optionally substituted by 1, 2 or 3 identical or different radicals, these radicals being $(C_1-C_4)$-alkyl, $(C_1-C_4)$-alkoxy, $(C_1-C_4)$-haloalkyl, $(C_1-C_4)$-haloalkoxy and/or halogen, or $R^2$ and $R^3$ together with the carbon atoms to which they are bonded form a saturated 5-, 6- or 7-membered isocyclic ring which can contain one or more oxygen or sulfur atoms instead of $CH_2$ and which is optionally substituted by one to four identical or different radicals selected from the series consisting of $(C_1-C_4$-alkyl and halogen, X is oxygen, NH and $S(O)_q$, it being possible for q to be 0, 1 or 2, $R^4$ is halogen, $(C_1-C_4)$-alkyl, $(C_3-C_4)$-cycloalkyl, $(C_1-C_4)$-haloalkyl, $(C_1-C_4)$-alkoxy, $(C_1-C_4)$-haloalkoxy or optionally substituted phenyl, p is an integer from 0 to 4, n is an integer from 0 to 2 and m can be an integer from 1 to 3, Y can be

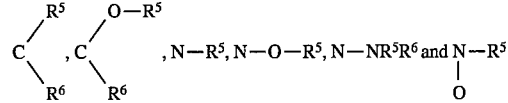

$R^5$ is hydrogen, halogen, $(C_1-C_{12})$-alkyl, $(C_3-C_8)$-cycloalkyl, $(C_3-C_8)$-cycloalkyl-$(C_1-C_4)$-alkyl, $[(C_1-C_4)$-alkoxy$]_t$-$(C_1-C_4)$-alkyl, it being possible for t to be an integer from 1 to 3, $(C_1-C_{12})$-haloalkyl, 2-(tetrahydro-2H-pyran-2-yloxy)-$(C_1-C_4)$-alkyl, $[(C_1-C_4)$haloalkoxy$]_t$-$(C_1-C_4)$-haloalkyl, $[(C_1-C_4)$-haloalkoxy$]_t$-$(C_1-C_4)$-alkenyl, $(C_1-C_8)$-alkylcarbonyl, $(C_1-C_8)$-alkoxycarbonyl, $(C_1-C_8)$-alkylcarbonyl-$(C_1-C_4)$-alkyl, $(C_1-C_8)$-haloalkylcarbonyl, $(C_1-C_8)$-haloalkoxycarbonyl, $(C_3-C_8)$-cycloalkylcarbonyl, $(C_3-C_8)$-cycloalkoxycarbonyl, optionally substituted benzoyl, optionally substituted benzyloxycarbonyl, $(C_2-C_8)$-alkenyl, $(C_2-C_8)$-alkynyl, tri-$(C_1-C_8)$-alkylsilyl, preferably dimethyl-$(C_1-C_8)$-alkylsilyl or triethylsilyl, di-$(C_1-C_8)$-alkyl-$(C_3-C_8)$-cycloalkylsilyl, preferably dimethylcyclohexylsilyl, di-$(C_1-C_8)$-alkyl-(phenyl-$C_1-C_4)$-alkyl)-silyl, preferably dimethyl-(phenyl-$(C_1-C_4)$-alkyl)-silyl, di-$(C_1-C_8)$-alkyl-$(C_1-C_4)$-haloalkylsilyl, dimethylphenylsilyl, heteroaryl, phenyl, phenyl-$(C_2-C_4)$-alkyl, benzyl, benzyloxy-$(C_1-C_4)$-alkyl, it being possible for phenyl or heteroaryl in the last-mentioned six radicals to be unsubstituted or mono- or polysubstituted, preferably up to trisubstituted, and these substituents, which are identical or different, are in each case halogen, $(C_1-C_8)$-alkyl, $(C_3-C_8)$-cycloalkyl, $(C_1-C_4)$-haloalkyl, $(C_1-C_4)$-dialkylamino, $(C_1-C_4)$-alkylthio, $(C_1-C_8)$-alkoxy, $(C_1-C_8)$-alkoxycarbonyl, $(C_1-C_8)$-alkanoyloxy, $(C_1-C_4)$-haloalkoxy, $(C_1-C_4)$-alkoxy-$(C_1-C_4)$-alkoxy, $[(C_1-C_4)$-alkyl-O$]_t$-$(C_2-C_4)$-alkyl, 2-(tetrahydro-2H-pyran-2-yloxy)-ethoxy, $(C_2-C_8$-alkenyl, $(C_2-C_8)$-alkynyl, phenoxy or benzyloxy which has optionally one or more, preferably up to three, identical or different substituents selected from the series consisting of $(C_1-C_4)$-alkyl, $(C_1-C_4)$-haloalkyl, $(C_1-C_4)$-alkoxy, $(C_1-C_4)$-haloalkoxy and halogen in the phenyl radical, $R^6$ is hydrogen, halogen, $(C_1-C_8)$-alkyl, $(C_3-C_8)$-cycloalkyl, $(C_1-C_8)$-haloalkyl, phenyl and benzyl, it being possible for the phenyl rings to be substituted as described above under $R^5$, or $R^5$ and $R^6$ together can form a 3- to 7-membered ring which can optionally be substituted by one, two or three identical or different radicals selected from the series consisting of halogen, $(C_1-C_4)$-alkyl, $(C_1-C_4)$-alkoxy, $(C_1-C_4)$-haloalkyl and $(C_1-C_4)$-haloalkoxy and in which a carbon atom can be replaced by O, S, $NR^7$ where $R^7$ is as defined for $R^4$ but must not be halogen.

In most cases, the compounds are in the form of enantiomers, diastereomers, for example E/Z isomers, or mixtures of these. The invention embraces both the pure isomers and their mixtures.

Preferred compounds of the formula I are those in which

A is as defined under formula I, $R^1$ is hydrogen or methyl, $R^2$ is halogen, $(C_1-C_4)$-alkyl, $(C_1-C_4)$-haloalkyl, $(C_1-C_4)$-alkoxy or $(C_1-C_4)$-alkoxy-$(C_1-C_4)$-alkyl, $R^3$ is hydrogen, halogen, $(C_1-C_3)$-alkyl, methoxy or ethoxy, or $R^2$ and $R^3$ together with the carbon atoms to which they are bonded form an unsaturated 5- or 6-membered ring which can contain one to two nitrogen atoms, an oxygen atom or a sulfur atom, or $R^2$ and $R^3$ together with the carbon atoms to which they are bonded form a saturated, optionally substituted 5- or 6-membered ring which can contain a sulfur atom or 1 to 2 oxygen atoms, and $R^4$, $R^5$, $R^6$ and $R^7$ and X, Y, m, n, p are as defined above.

Particularly preferred compounds of the formula I are those in which

A is as defined under the formula I, $R^1$ is hydrogen, $R^2$ is $(C_1-C_4)$-alkyl or methoxymethyl, $R^3$ is methyl, ethyl, methoxy, chlorine or bromine, or $R^2$ and $R^3$ together with the carbon atoms to which they are bonded form the quinoline or quinazoline system which can be substituted by fluorine, chlorine, bromine or methyl, or $R^2$ and $R^3$ together with the carbon atoms to which they are bonded form an unsaturated 6-membered ring which contains a nitrogen atom, or $R^2$ and $R^3$ together with the carbon atoms to which they are bonded form a saturated 6-membered ring which can contain one or two oxygen atoms, m, n, p and X are as defined above, Y can be

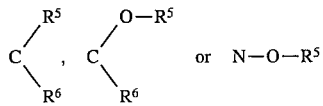

and $R^5$, $R^6$ and $R^7$ are also as already defined above

Particularly preferred compounds of the formula I are furthermore those in which A and $R^1$ to $R^7$ are as defined above and m and n are 2, p is 0, and X is NH or an oxygen atom.

Very particularly preferred compounds of the formula I are those in which

A is as defined under formula I, $R^1$ is hydrogen, $R^2$ is $(C_1-C_4)$-alkyl or methoxymethyl, $R^3$ is chlorine, bromine or methoxy, or $R^2$ and $R^3$ together with the carbon atoms to which they are bonded form the quinoline or quinazoline system which can be substituted by fluorine, chlorine, bromine or methyl, or $R^2$ and $R^3$ together with the pyrimidine ring form the 5,6,7,8-tetrahydroquinazoline system or the 5,6-dihydro-7H-pyrano[2,3-d]pyrimidine system, m and n are the number two and p is zero, X is NH or an oxygen atom, Y is

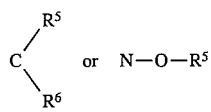

$R^5$, $R^6$ and $R^7$ are as already defined above.

Very particularly preferred compounds of the formula I are furthermore those in which A is as defined under formula I, $R^1$ is hydrogen, $R^2$ is methoxymethyl and $R^3$ is methoxy, or $R^2$ is $(C_1-C_4)$-alkyl and $R^3$ is chlorine or bromine, or $R^2$ and $R^3$ together with the carbon atom to which they are bonded form a quinoline or quinazoline system which is substituted by fluorine, chlorine or methyl, or a 5,6,7,8-tetrahydroquinazoline system or the 5,6-dihydro-7H-pyrano[2,3-d]pyrimidine system, m, n, p, X and Y are as defined above, $R^5$ is $(C_2-C_8)$-alkyl, cyclopentyl, cyclohexyl, $(C_1-C_8)$-alkylcarbonyl, $(C_1-C_8)$-alkoxycarbonyl, phenyl, benzyl or benzoyl, it being possible for the last-mentioned three radicals to be unsubstituted or to be provided with one or two substituents which can be identical or different and are fluorine, chlorine, bromine, $(C_1-C_4)$-alkyl, $(C_1-C_4)$-alkoxy, trifluoromethyl, $(C_1-C_2)$-haloalkoxy, cyclohexyl, 2-ethoxyethoxy, methylthio or dimethylamino, and $R^6$ can be H, halogen or $(C_1-C_3)$-alkyl.

In the above formula I, "halogen" is to be understood as meaning a fluorine, chlorine, bromine or iodine atom, preferably a fluorine, chlorine or bromine atom, the term "$(C_1-C_4)$-alkyl" is to be understood as meaning an unbranched or branched hydrocarbon radical having 1–4 hydrocarbon atoms, such as, for example, the methyl, ethyl, propyl, 1-methylethyl, 1-methylpropyl, 2-methylpropyl or 1,1-dimethylethyl radical, the term "$(C_1-C_8)$-alkyl" is to be understood as meaning the abovementioned alkyl radicals and, for example, the pentyl, 2-methylbutyl or the 1,1-dimethylpropyl radical, or the hexyl, heptyl, octyl or 1,1,3,3-tetramethylbutyl radical;

the term "$(C_1-C_{12})$-alkyl" is to be understood as meaning the abovementioned alkyl radicals and, for example, the nonyl, decyl undecyl or dodecyl radical;

the term "$(C_3-C_8)$-cycloalkyl" is to be understood as meaning the cyclopropyl, cyclobutyl, cyclopentyl, cyclohexyl, cycloheptyl or cyclooctyl group;

the term "$(C_1-C_4)$-alkoxy" is to be understood as meaning an alkoxy group whose hydrocarbon radical is as defined under the term "$(C_1-C_4)$-alkyl";

the term "$(C_3-C_8)$-cycloalkoxy" is to be understood as meaning a cycloalkoxy group whose hydrocarbon radical is as defined under "$(C_1-C_4)$-cycloalkyl";

the term "$(C_1-C_4)$-alkylthio" is to be understood as meaning an alkylthio group whose hydrocarbon radical is as defined under the term "$(C_1-C_4)$-alkyl";

the term "$(C_1-C_4)$-haloalkoxy" is to be understood as meaning a haloalkoxy group whose halogenated hydrocarbon radical is as defined under the term "$(C_1-C_4)$-haloalkyl";

the term "$(C_1-C_4)$-alkoxy-$(C_1-C_4)$-alkyl" is to be understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the term "$(C_1-C_4)$-alkylthio-$(C_1-C_4)$-alkyl" is to be understood as meaning, for example, methylthio, ethylthiomethyl, propylthiomethyl, 2-methylthioethyl, 2-ethylthioethyl or 3-methylthiopropyl;

the term "$(C_1-C_4)$-alkylamino" is to be understood as meaning an alkylamino group whose hydrocarbon radical is as defined under the term "$(C_1-C_4)$-alkyl", preferably the ethyl- or methylamino group;

the term "di-$(C_1-C_4)$-alkylamino" is to be understood as meaning a dialkylamino group whose hydrocarbon radicals are as defined under the term "$(C_1-C_4)$-alkyl", preferably the dimethylamino or diethylamino group;

the term "$(C_1-C_4)$-haloalkyl" is to be understood as meaning an alkyl group mentioned under the term "$(C_1-C_4)$-alkyl" in which one or more hydrogen atoms are replaced by the abovementioned halogen atoms, preferably chlorine or fluorine, such as, for example, the trifluoromethyl group, the 2,2,2-trifluoroethyl group, the chloromethyl or fluoromethyl group, the difluoromethyl group or the 1,1,2,2-tetrafluoroethyl group;

the term "$(C_3-C_8)$-cycloalkyl-$(C_2-C_4)$-alkyl" is to be understood as meaning one of the abovementioned $(C_1-C_4)$-alkyl groups which is substituted by one of the abovementioned $(C_3-C_8)$-cycloalkyl groups, for example cyclohexylmethyl, cyclohexylethyl, cyclohexylpropyl, cyclohexylbutyl or 1-cyclohexyl-1-methylethyl;

the term "phenyl-$(C_1-C_4)$-alkyl" is to be understood as meaning one of the abovementioned $(C_1-C_4)$-alkyl groups which is substituted by a phenyl group, for example the benzyl, the 2-phenylethyl, the 1-phenylethyl, the 1-methyl-1-phenylethyl, the 3-phenylpropyl, the 4-phenylbutyl or the 2-methyl-2-phenyl-ethyl group;

the term "aryl" is to be understood as meaning, for example, phenyl, naphthyl or biphenyl, preferably phenyl; the term "optionally substituted phenyl", unless otherwise defined specifically, is to be understood as meaning a phenyl radical which has one, two or three identical or different substituents selected from the series consisting of halogen, $(C_1-C_4)$-alkyl, $(C_1-C_4)$-alkoxy, $(C_1-C_4)$-haloalkyl and $(C_1-C_4)$-haloalkoxy;

the term "optionally substituted benzoyl" is to be understood as meaning a radical in which the phenyl moiety is substituted as in "optionally substituted phenyl";

the term "optionally substituted benzoylcarbonyl" is to be understood as meaning a radical in which the phenyl moiety is substituted as in "optionally substituted phenyl";

the term "heteroaryl" is to be understood as meaning an aryl radical in which at least one CH group is replaced by N and/or at least two adjacent CH groups are replaced by S, NH or O; examples of such radicals are thienyl, benzothienyl, furyl, benzofuryl, pyrrolyl, imidazolyl, pyrazolyl, pyridyl, pyrazinyl, pyrimidinyl, pyridazinyl, indolizinyl, isoindolyl, indolyl, indazolyl, purinyl, quinolyl, isoquinolyl, phthalazinyl, naphthydrinyl, quinoxalinyl, quinazolinyl, cinnolinyl, pteridinyl, oxazolyl, isoxazolyl, thiazolyl, isothiazolyl, tetrazolyl;

the term "benzyloxy-$(C_1-C_4)$-alkyl" is to be understood as meaning a $(C_1-C_4)$-alkyl group as defined above which is substituted by a benzyloxy group, for example the benzyloxymethyl or the 2-(benzyloxy)-ethyl group;

the term "$(C_3-C_8)$-cycloalkyl-$(C_1-C_4)$-alkoxy" is to be understood as meaning a $(C_1-C_4)$-alkoxy group which is as defined above and which is substituted by a $(C_3-C_8)$-cycloalkyl group as defined above, for example the cyclopropylmethyloxy or the cyclohexylmethyloxy group;

the term "tri-$(C_1-C_4)$-alkylsilyl" is to be understood as meaning a trialkylsilyl group which has preferably two methyl groups and one $(C_1-C_8)$-alkyl group as defined above, for example the trimethylsilyl, the dimethylethylsilyl or the dimethyloctylsilyl group;

the term "di-$(C_1-C_8)$-alkyl-$(C_1-C_4)$-haloalkylsilyl" is to be understood as meaning a silyl radical which has preferably two methyl groups and one $(C_1-C_4)$-haloalkyl radical, where the term $(C_1-C_4)$-haloalkyl is as defined above, for example the dimethyl-3,3,3-trifluoropropylsilyl radical;

the term "$(C_1-C_4)$-alkoxy-$(C_1-C_4)$-alkoxy" is to be understood as meaning, for example, the ethoxymethoxy, 2-ethoxyethoxy, 2-butoxyethoxy or 2-methoxyethoxy group;

the term "$(C_3-C_8)$-alkenyl" is to be understood as meaning an unbranched or branched radical, such as the vinyl, allyl, 2-butenyl, 2-pentenyl or 2-hexenyl group;

the term "$(C_2-C_8)$-alkynyl" is to be understood as meaning, for example, the propargyl, 2-butynyl or 2-pentynyl group;

the term "$(C_1-C_8)$-alkanoyl" is to be understood as meaning an unbranched or branched radical, such as formyl, acetyl, propionyl, butyryl, isobutyryl, valeryl, isovaleryl, pivaloyl, caproyl or octanoyl;

the term "tri-$(C_1-C_4)$-alkylsilylmethoxy" is to be understood as meaning a trialkylsilylmethoxy radical having preferably 2 methyl groups, in which the $(C_1-C_4)$-alkyl group is as defined above;

the term "di-$(C_1-C_8)$-alkyl-phenyl-$(C_1-C_4)$-alkylsilyl" is to be understood as meaning a trialkylsilyl radical having preferably two methyl groups, in which one alkyl group is as defined above under the term "phenyl-$(C_1-C_4)$-alkyl", preferably the dimethylbenzylsilyl group.

The explanation given above applies analogously to homologous radicals or to radicals derived from the abovementioned radicals.

The present invention relates to the compounds of the formula I in the form of the free base or of an acid addition salt. Acids which can be used to form salts are inorganic acids, such as hydrochloric acid, hydrobromic acid, nitric acid, sulfuric acid, phosphoric acid, or organic acids, such as formic acid, acetic acid, propionic acid, oxalic acid, fumaric acid, adipic acid, stearic acid, oleic acid, methanesulfonic acid, benzenesulfonic acid or toluenesulfonic acid.

Some of the compounds of the formula I have one or more elements of chirality. Racemates and diastereomers can therefore occur. The invention embraces both the pure isomers and also mixtures of these. The mixtures of diastereomers can be resolved to give the components by customary methods, for example by selective crystallization from suitable solvents or by chromatography. Racemates can be resolved to give the enantiomers by customary methods, for example by forming salts with an optically active acid, resolution of the diastereomeric salts and liberation of the pure enantiomers by means of a base.

The invention furthermore relates to a process for the preparation of compounds of the formula I, which comprises reacting a compound of the formula II

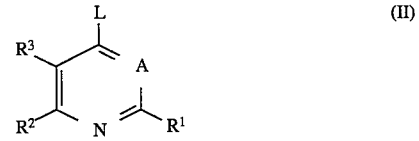

in which A, , $R^1$, $R^2$ and $R^3$ are as defined under formula I and L is a leaving group, for example halogen, alkylthio, alkanesulfonyloxy or arylsulfonyloxy, alkylsulfonyl or arylsulfonyl, with a nucleophile of the formula III

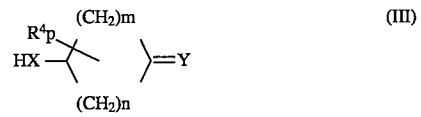

in which X, $R^4$, n, m and Y are as defined under formula I, and, if appropriate, in the event that $R^3$ is hydrogen and A is nitrogen, the $C^5$ of the pyrimidine in the resulting compounds of the formula I is chlorinated or brominated.

The substitution reaction described above is known in principle. The leaving group L can be varied within wide limits and can be, for example, a halogen atom, such as fluorine, chlorine, bromine or iodine, or alkylthio, such as methylthio or ethylthio, or alkanesulfonyloxy, such as methane-, trifluoromethane- or ethanesulfonyloxy, or arylsulfonyloxy, such as benzenesulfonyloxy or toluenesulfonyloxy, or alkanesulfonyl, such as methylsulfonyl or ethylsulfonyl, or arylsulfonyl such as phenylsulfonyl or toluenesulfonyl.

The abovementioned reaction is carried out in a temperature range of 20°–150° C., expediently in the presence of a base and, if appropriate, in an inert organic solvent, such as N,N-dimethylformamide, N,N-dimethylacetamide, dimethyl sulfoxide, N-methylpyrrolidine-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

Examples of suitable bases are the carbonates, hydrogen carbonates, amides or hydrides of alkali metals or alkaline earth metals, such as sodium carbonate, sodium hydrogen carbonate, potassium carbonate, sodium amide or sodium hydride, or organolithium compounds, such as n-butyllithium.

In the event that X is oxygen, then examples of suitable bases are the carbonates, hydrogen carbonates, amides or hydrides of alkali metals or alkaline earth metals, such as sodium carbonate, sodium hydrogen carbonate, potassium carbonate, sodium amide or sodium hydride, in the event that X is NH, examples of suitable bases are the carbonates, hydrogen carbonates, hydroxides, amides or hydrides of alkali metals or alkaline earth metals, such as sodium carbonate, sodium hydrogen carbonate, potassium carbonate, sodium hydroxide, sodium amide or sodium hydride, or organic bases, such as triethylamine or pyridine. It is also possible to use the second equivalent of an amine III as auxiliary base.

The invention furthermore relates to a process for the preparation of compounds of the formula V which comprises converting a compound of the formula IV

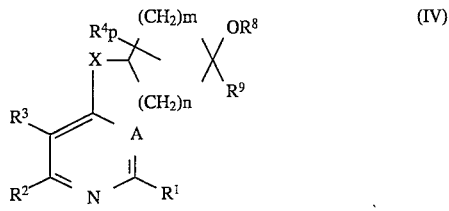

in which A, $R^1$, $R^2$, $R^3$, $R^4$, X, n, m and p are as defined under formula I and $R^8$ and $R^9$ are identical or different and are hydrogen, $(C_1-C_8)$-alkyl or $(C_1-C_8)$-haloalkyl, or $R^8$ and $R^9$ together form a saturated 5-, 6- or 7-membered isocyclic ring which is optionally monosubstituted or polysubstituted, preferably up to trisubstituted, by identical or different radicals, such as $(C_1-C_4)$-alkyl, benzyl or phenyl, using an inorganic or organic acid, such as, for example, HCl, $H_2SO_4$, $HNO_3$, $H_3PO_4$, oxalic acid, acetic acid or an acidic ion exchanger, into a compound of the formula V

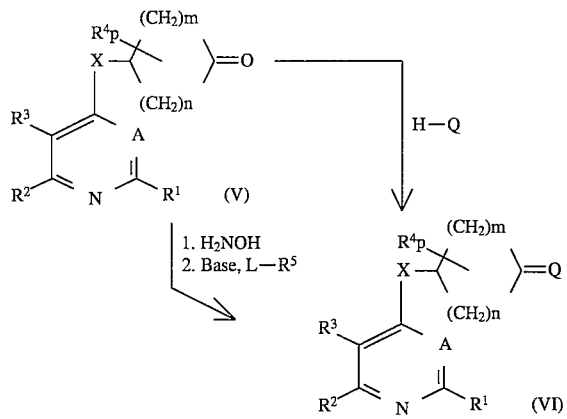

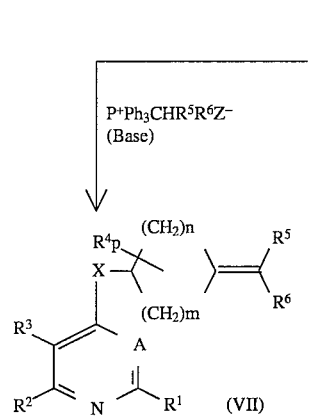

in which the radicals A, $R^2$, $R^3$, X, $R^5$, $R^6$, $R^7$, m and p are as defined under formula I, Q is $HNR^5$, $HNOR^5$, $HN-NR^5R^6$ or $N(OH)R^5$, Ph is an aromatic radical, preferably phenyl, and $Z^-$ is an anion, preferably halide, such as iodide. Compounds of the formula IV have already been described in DE-A 4116089. In the event that $R^2$ and $R^3$ form an unsaturated 5- or 6-membered isocyclic ring which can also contain one or more nitrogen atoms and which is optionally substituted by 1, 2 or 3 identical or different radicals, and these radicals are $(C_1-C_4)$-alkyl, $(C_1-C_4)$-alkoxy, $(C_1-C_4)$-haloalkyl, $(C_1-C_4)$-haloalkoxy and/or halogen, compounds of the formula IV are new and are a subject of the invention.

Compounds of the formula V are starting compounds for the preparation of compounds of the formulae VI and VII, which are prepared by processes analogous to known processes, Z preferably being a halogen atom, in particular Cl, Br or I. The compounds of the formula V are also novel, and are a subject of the invention.

$H_2NOH$ and compounds of the formula HQ can be employed as the free bases or in the form of their acid addition salts. $H_2NOH$ or HQ is liberated from the latter in situ by adding a base. Bases which are suitable for this purpose are hydroxides, carbonates, hydrogen carbonates, acetates or alcoholates of alkali metals or alkaline earth metals, such as sodium hydroxide, sodium carbonate, sodium acetate, sodium hydrogen carbonate or potassium carbonate, or organic bases such as triethylamine or pyridine.

The abovementioned reactions which lead to compounds of the formula VI are carried out in a temperature range of −20° to −150° C., and, if appropriate, in an inert organic solvent, such as N,N-dimethylformamide, N,N-dimethylacetamide, dimethyl sulfoxide, N-methylpyrrolidine-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

The abovementioned reactions which lead to compounds of the formula VII are carried out in an inert organic solvent or solvent mixture from the series of the abovementioned solvents and solvent mixtures in the presence of a base at a temperature between −80° C. and the boiling point of the reaction mixture, preferably between 10° and 70° C. Examples of suitable bases are hydroxides, alcoholates, carbonates, amides or hydrides of alkali metals or alkaline earth metals, such as sodium hydroxide, sodium ethanolate, sodium carbonate, potassium carbonate, sodium amide or sodium hydride, or organolithium compounds such as n-butyllithium.

The starting compounds of the formula II are either known or can be prepared analogously to known processes; see, for example:

Quinolines: *Org. Synth., Coll. Vol.* 3, 272 (1955)
1,5-Naphthyridines: *J. Amer. Chem. Soc.* 68, 1317 (1946) and
British Patent 1147760
1,6-Naphthyridines: *J. Chem. Soc.* 1960, 1790
1,7-Naphthyridines: *J. Org. Chem.* 19, 2008 (1954)
1,8-Naphthyridines: *Synthesis* 1974, 809
Pyridopyrimidines: EP-A-414 386
Pteridines: *J. Chem. Soc.* 1951, 474

In the event that A is a nitrogen atom, then acetoacetate derivatives, which are converted into the halopyrimidines via the corresponding hydroxypyrimidines, are used as starting materials:

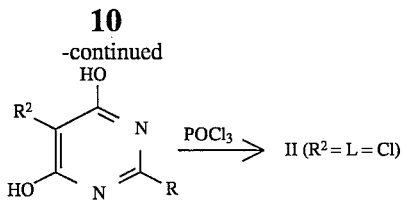

In the event that X is oxygen, the nucleophiles of the formula III, which are required as starting materials, can be prepared by known processes, for example by reducing a carbonyl group with a suitable reducing agent, for example a complex metal hydride, or alternatively, in the case of an aldehyde or ketone, with hydrogen and a hydrogenation catalyst. Other possibilities are reaction of an organometallic compound with a carbonyl group or an oxirane.

In the event that X is NH, the nucleophiles of the formula III, which are required as starting materials, can also be prepared by known methods, for example by reduction of an oxime with a suitable reducing agent, for example a complex metal hydride or hydrogen in the presence of a hydrogenation catalyst, reductive amination or Leuckart-Wallach reac-

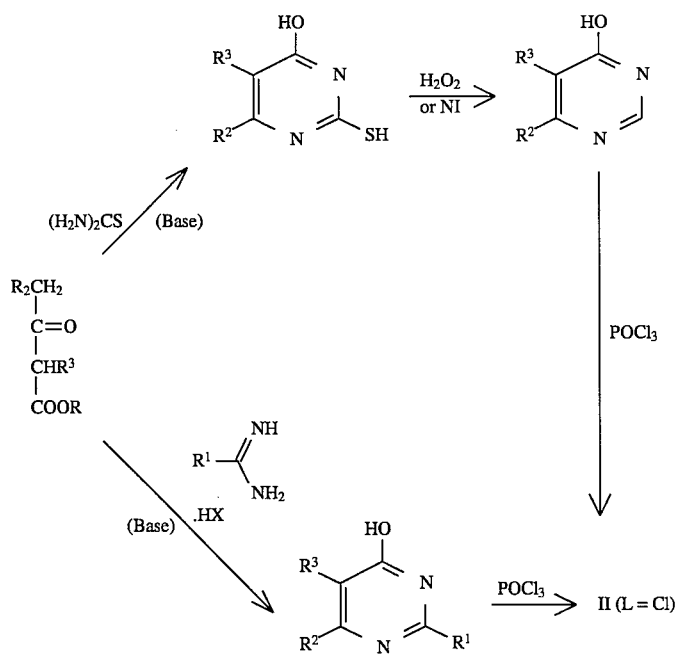

In the event that $R^2$ and $R^3$ together with the carbon atoms to which they are bonded form a saturated 5-, 6- or 7-membered isocyclic ring which can contain one or more oxygen or sulfur atoms instead of $CH_2$ and which is optionally substituted by one to four $(C_1-C_4)$-alkyl groups and/or halogen, the compounds of the formula II are novel and are claimed.

The starting compounds of the formula II can furthermore be obtained from malonate derivatives analogously to known processes:

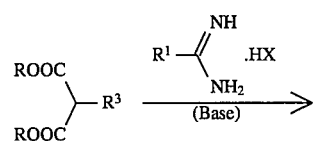

tion of an aldehyde or ketone, or Gabriel reaction of an alkyl halide or alkyl tosylate.

The compounds of the formula I in which $R^3$ is halogen can be halogenated by known processes.

The compounds of the formula I according to the invention are distinguished by an outstanding fungicidal activity. Fungal pathogens which have already penetrated the plant tissue can successfully be controlled in a curative manner. This is particularly important and advantageous in the case of those fungal diseases which can no longer be controlled effectively with the otherwise customary fungicides once infection has taken place. The spectrum of action of the claimed compounds extends to a range of economically important phytopathogenic fungi but, in particular, to *Erysiphe graminis* and *Leptosphaeria nodorum*.

In addition, the compounds according to the invention are also suitable for use in industrial areas, for example as wood preservatives, as preservatives in paints, in cooling lubricants for metalworking, or as preservatives in drilling and cutting oils.

The invention also relates to compositions which contain the compounds of the formula I in addition to suitable formulation auxiliaries. The compositions according to the invention generally contain 1 to 95% of the active substances of the formula I. They can be formulated in various ways, depending on the prevailing biological and/or chemico-physical parameters. Suitable formulations which are possible are therefore the following: wettable powders (WP), emulsifiable concentrates (EC), oil- or water-based aqueous dispersions (SC), suspoemulsions (SC), dusts (DP), seed dressing products, granules in the form of water-dispersible granules (WG), ULV formulations, microcapsules, waxes or baits.

These individual types of formulations are known in principle and are described, for example, in: Winnacker-Küchler, "Chemische Technologie" [Chemical Technology], Volume 7, C. Hauser Verlag, Munich, 4th Edition 1986; yon Falkenberg, "Pesticides Formulations", Marcel Dekker N.Y., 2nd Ed. 1972–73; K. Martens, "Spray Drying Handbook", 3rd Ed. 1979, G. Goodwin Ltd., London.

The formulation auxiliaries required, such as inert materials, surfactants, solvents and other additives, are also known and are described, for example, in:

Watkins, "Handbook of Insecticide Dust Diluents and Carrier", 2nd Ed., Darland Books, Caldwell N.J.; H. v. Olphen, "Introduction to Clay Colloid Chemistry", 2nd Ed., J Wiley & Sons, N Y.; Marschen, "Solvents Guide", 2nd Ed., Interscience, N.Y. 1950; McCutcheon's "Detergents and Emulsifiers Annual", MC Publ. Copr., Ridgewood N.J.; Sisley and Wood, "Encyclopaedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag, Munich, 4th Edition 1986.

Based on these formulations, combinations with other pesticidally active substances, fertilizers and/or growth regulators can also be prepared, for example in the form of readymix or a tankmix.

Wettable powders are preparations which are uniformly dispersible in water and which contain, beside the active substance, wetting agents, for example polyoxethylated alkylphenols, polyoxethylated fatty alcohols, alkylsulfonates or alkylphenolsulfonates, and dispersants, for example sodium ligninsulfonate, sodium 2,2'-dinaphthylmethane-6,6'-disulfonate, sodium dibutylnaphthalenesulfonate or else sodium oleylmethyltaurinate, in addition to a diluent or inert substance. Emulsifiable concentrates are prepared by dissolving the active substance in an organic solvent, for example butanol, cyclohexanone, dimethylformamide, xylene or else higher-boiling aromatics or hydrocarbon atoms, with an addition of one or more emulsifiers. Examples of emulsifiers which can be used are:

Calcium alkylarylsulfonate, such as calcium dodecylbenzenesulfonate, or nonionic emulsifiers, such as fatty acid polyglycol esters, alkyl aryl polyglycol ethers, fatty alcohol polyglycol ethers, polyoxyethylene-polyoxypropylene eorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite, pyrophillite or diatomaceous earth. Granules can be prepared either by spraying the active substance onto absorptive, granulated inert material or by applying active substance concentrates to the surface of carriers, such as sand, kaolinites or granulated inert material with the aid of binders, for example polyvinyl alcohol, sodium polyacrylate or else mineral oils. Suitable active substances can also be granulated in the manner customary for the preparation of fertilizer granules, if desired in the form of a mixture with fertilizers.

The active substance concentration in wettable powders is, for example, approximately 10 to 90% by weight, the remainder to 100% by weight is composed of customary formulation auxiliaries. In the case of emulsifiable concentrates, the active substance concentration can be approximately 5 to 80% by weight. Formulations in the form of dusts usually contain 5 to 20% by weight. In the case of granules, the active substance content depends partly on whether the active compound is in liquid or solid form and on which granulation auxiliaries, fillers and the like are being used.

In addition, the abovementioned formulations of active substances contain, if appropriate, the adhesives, wetting agents, dispersants, emulsifiers, penetrants, solvents, fillers or carriers which are customary in each case.

For use, the concentrates which are in commercially available form are, if appropriate, diluted in the customary manner, for example using water in the case of wettable powders, emulsifiable concentrates, dispersions and also in the case of some microgranules.

Preparations in the form of dusts and granulated preparations and sprayable solutions are conventionally not diluted any further with other inert substances before use.

The application rate required varies with the external conditions, such as temperature, humidity and the like. It can vary within wide limits, for example between 0.005 and 10 kg/ha or more of active ingredient, but it is preferably between 0.01 and 5 kg/ha.

The active substances according to the invention can be used in their commercially available formulations either by themselves or in combination with other fungicides known from the literature.

Fungicides which are known from the literature and which can be combined according to the invention with the compounds of the formula I which may be mentioned are, for example, the following products:

aldimorph, andoprim, anilazine, BAS 480F, BAS 490F, benalaxyl, benodanil, benomyl, binapacryl, bitertanol, bromuconazole, buthiobate, captafol, captan, carbendazim, carboxin, CGA 173506, chlobenzthiazone, chlorthalonil, cymoxanil, cyproconazole, cyprofuram, dichlofuanid, dichlomezin, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF 164), fluazinam, fluobenzimine, fluquinconazole, fluorimide, flusilazole, flutolanil, flutriafol, folpet, fosetyl-aluminum, fuberidazole, fulsulfamide (MT-F651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconazole, mepronil, metalaxyl, methasulfocarb, methfuroxam, MON 24000, myclobutanil, namab, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiophanate-methyl, thiram, tolclofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/ C15-alcohol ether sulfonate, sodium cetostearyl phosphate, sodium dioctyl sulfous oxinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkyl-imidazoline.

The abovementioned components are known active substances, many of which are described in Ch. R. Worthing, U.S.B. Walker, The Pesticide Manual, 7th Edition (1983), British Crop Protection Council.

Moreover, the active substance according to the invention can exist in its commercially available formulations and in the use forms prepared with these formulations in the form of a mixture with other active substances, such as insecticides, attractants, sterilants, acaricides, nematicides or herbicides. The insecticides include, for example, phosphoric esters, carbamates, carboxylic esters, formamidines, tin compounds, substances produced by microorganisms and the like. The following are preferred components in mixtures:

1. From the group of the phosphorus compounds acephate, azamethiphos, azinphos-ethyl, azinphosmethyl, bromophos, bromophos-ethyl, chlorfenvinphos, chlormephos, chlorpyrifos, chlorpyrifosmethyl, demeton, demeton-S-methyl, demeton-S-methylsulfone, dialifos, diazinon, dichlorvos, dicrotophos, O,O-1,2,2,2-tetrachlorethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isophos, isothioate, isoxathion, malathion, methacrifos, methamidophos, methidathion, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalfos, sulprofos, temephos, terbufos, tetrachlorvinphos, thiometon, triazaphos, trichlorphon, vamidothion.

2. From the group of the carbamates aldicarb, 2-sec.-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyrylmethylcarbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methyl-thio(ethylideneamino)-N-methyl-N-(morpholinothio)carbamate (UC 51717).

3. From the group of the carboxylic esters allethrin, alphametrin, 5-benzyl-3-furylmethyl (E)-(1R)-cis-2,2-dimethyl-3-(2-oxothiolan-3-ylidene-methyl)cyclopropanecarboxylate, bioallethrin, bioallethrin((S)-cyclopentylisomer),bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cypermethrin, cyphenothrin, deltamethrin, empenthrin, esfenvalerate, fentfluthrin, fenpropathrin, fenvalerate, flucythrinate, flumethrin, fluvalinate (D isomer), permethrin, pheothrin ((R) isomer), d-prallethrin, pyrethrines (natural products), resmethrin, tefluthrin, tetramethrin, tralomethrin.

4. From the group of the amidines amitraz, chlordimeform.

5. From the group of the tin compounds cyhexatin, fenbutatin oxide.

6. Others abamectin, Bacillus thuringiensis, bensultap, binapacryl, bromopropylate, buprofezin, camphechlor, cartap, chlorobenzilate, chlorfluazuron, 2-(4-(chlorphenyl)-4, 5-diphenylthiophene (UBI-T 930), chlorfentezine, 2-naphthylmethyl cyclopropane carboxylate (Ro12-0470), cyromazin, ethyl N-(3,5-dichloro-4-(1,1,2,3,3, 3-hexafluoro-1-propyloxy)-phenyl)carbamoyl)-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)-(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro6H-thiazin (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron.

The active substance content of the use forms prepared with the commercially available formulations can vary within broad limits, the active substance concentration in the use forms can be from 0.0001 up to 95% by weight of active substance, preferably between 0.001 and 1% by weight. They are applied in a customary manner which suits the use forms.

The active substances are well tolerated by plants, have a favorable toxicity to warm-blooded species and are suitable for controlling animal pests, in particular insects, arachnids, helminths and molluscs, very particularly preferably for controlling insects and arachnids which occur in agriculture, in livestock breedings, in forests, in the protection of stored products and of materials, and in the hygiene sector. They are active against normally sensitive and resistant species and against all or individual development stages. The abovementioned pests include:

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp..

From the order of the Isopoda, for example, *Oniscus asellus,* Armadillidiumvulgare and *Porcellio scaber.*

From the order of the Diplopoda, for example, *Blaniulus guttulatus.*

From the order of the Chilopoda, for example, *Geophilus carpophagus* and Scutigera spp..

From the order of the Symphyla, for example, *Scutigerella immaculata.*

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Isoptera, for example, Reticulitermes spp..

From the order of the Anoplura, for example, *Phylloxera vastatrix*, Pemphigus spp., *Pediculus humanus corporis*, Haematopinus spp. and Linognathus spp..

From the order of the Mallophaga, for example, Trichodectes spp. and Damalinea spp..

From the order of the Thysanoptera, for example, *Bercinothrips femoralis* and *Thrips tabaci*.

From the order of the Beteroptera, for example, Eurygaster spp., *Dysdercus intermedius, Piesma quadrata, Cimex lectularius, Rhodnius prolixus* and Triatoma spp..

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp..

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonumus spp., Sitophilus spp., *Otiorrhynchus sulcatus, Cosmopolites sordidus, Ceuthorrhynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp..

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopsis* and Ceratophyllus spp..

From the order of the Arachnida, for example, *Scorpio maurus* and *Latrodectus mactans*.

From the class of the Helminthes, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola and plant-injurious nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, Deroceras spp., Arion spp., Lymnaea spp., Galba spp., Succinea spp., Biomphalaria spp., Bulinus spp. and Oncomelania spp..

From the class of the Bivalva, for example, Dreissena spp..

The invention also relates to compositions, in particular to insecticidal and acaricidal compositions, which contain the compounds of the formula I in addition to suitable formulation auxiliaries.

In general, the compositions according to the invention contain 1 to 95% by weight of the active substances of the formula I.

They can be formulated in various ways, depending on the prevailing biological and/or chemico-physical parameters.

The application rate required varies with the external conditions, such as temperature, humidity and the like. It can vary within wide limits, for example between 0.0005 and 10.0 kg/ha or more of active ingredient, but it is preferably between 0.001 and 5 kg/ha.

The active substances according to the invention can exist in their commercially available formulations and in the use forms prepared with these formulations in the form of mixtures with other active substances, such as insecticides, attractants, sterilants, acaricides, nematicides, fungicides, growth-regulating substances or herbicides.

The pesticides include, for example, phosphoric esters, carbamates, carboxylic esters, formamidines, tin compounds, substances produced on microorganisms and the like. The following are preferred components in mixtures:

1. From the group of the phosphorus compounds acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-Smethyl, demeton-S-methylsulfone, dialifos, diazinon, dichlorvos, dicrotophos, O,O-1,2,2,2-tetrachlorethyl phosphorthioate (SD 208 304), dimethoate, disulfoton, EPN, ethion, ethoprophos, etrimfos, famphur, fenamiphos, fenitrothion, fensulfothion, fenthion, fonofos, formothion, heptenophos, isozophos, isothioate, isoxathion, malathion, methacrifos, methamidophos, methidathion, dathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphosethyl, pirimiphos-methyl, profenofos, propaphos, proetamphos, prothiofos, pyraclosfos, pyridapenthion, quinalfos, sulprofos, temephos, terbufos, tetrachlorvinphos, thiometon, triazaphos, trichlorphon, vamidothion;

2. From the group of the carbamates aldicarb, 2-sec.-butylphenylmethylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl ( methyl ) carbamate, oxamyl, pirimicarb, propoxur, thiodicarb, thiofanox, ethyl-4,6,9-triaza-4-benzyl-6,10-dimethyl-8-oxa-7-oxo-5,11-dithia-9-dodecenoate (OK 135), 1-methylthio(ethylideneamino)-N-methyl-N-(morpholinthio)carbamate (UC 51717);

3. From the group of the carboxylic esters allethrin, alphametrin, 5-benzyl-3-furylmethyl (E)-(1R)-cis-2,2-dimethyl-3-(2-oxothiolan-3-ylidenemethyl)cyclopropane-carboxylate, bioallethrin, bioallethrin((S)-cyclopentyl isomer), bioresmethrin, biphenate, (RS)-1-cyano-1-(6-phenoxy-2-pyridyl)-methyl (1RS)-trans-3-(4-tert-butyl-phenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fentfluthrin, fenpropathrin, fenvalerate, flucythrinate, flumethrin, fluvalinate (D isomer), permethrin, pheothrin ((R) isomer), d-prallethrin, pyrethrins (natural products), resmethrin, tefluthrin, tetramethrin, tralomethrin;

4. From the group of the amidines amitraz, chlordimeform;

5. From the group of the tin compounds cyhexatin, fenbutatin oxide.

6. Others abamectin, *Bacillus thuringiensis*, bensultap, binapacryl, bromopropylate, buprofezin, camphechlor, cartap, chlorobenzilate, chlorfluazuron, 2-(4-(chlorphenyl)-4,5-diphenylthiophene (UBI-T 930), chlorfentezine, (2-naphthylmethyl)cyclopropane carboxylate (Ro12-0470), cyromazin, ethyl N-(3,5-dichloro-4-(1,1,2,3,3,3-hexafluoro-1-propyloxy)phenyl)carbamoyl)-2-chlorobenzocarboximidate, DDT, dicofol, N-(N-(3,5-dichloro-4(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazin (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron, imidacloprid.

The active substance content of the use forms prepared with the commercially available formulations can be from 0.00000001 up to 95% by weight of active substance, preferably between 0.00001 and 1% by weight.

They are used in a customary manner which suits the use forms.

The active substances according to the invention are also suitable for controlling endoparasites and ectoparasites in the field of veterinary medicine or in the field of animal-keeping.

Here, the active substances according to the invention are administered in a known manner, such as by oral administration in the form of, for example, tablets, capsules, drinks, granules, by dermal administration for example in the form of dipping, spraying, pouring on and spotting on, and dusting, and by parenteral administration, for example in the form of an injection.

Accordingly, the novel compounds of the formula I according to the invention can also be employed particularly advantageously in livestock breeding (for example cattle, sheep, pigs and poultry such as chickens, geese and the like).

In a preferred embodiment of the invention, the novel compounds, if appropriate in suitable formulations (cf. above) are administered to the animals orally, if appropriate together with the drinking water or feed. Since they are excreted highly effectively with the feces, this allows the development of insects in the feces of the animals to be prevented in a very simple manner. The dosage rates and formulations which are suitable in each case will depend, in particular, on the species and the development stage of the livestock and also on the severity of the infection, and they can be determined and decided easily by customary methods. In the case of cattle, for example, the novel compounds can be employed at dosage rates from 0.01 to 1 mg/kg of bodyweight.

The examples which follow are intended to illustrate the invention without restricting it thereto.

A. Preparation Examples

Example a 4-(4-Isobutylidenecyclohexylamino)-5-methoxy-6-methoxymethylpyrimidine

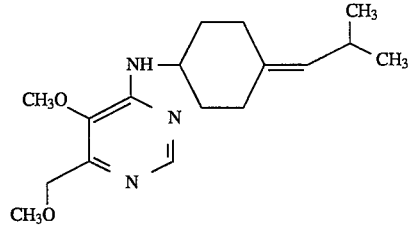

3.8 g (20 mmol) of 4-chloro-5-methoxy-6-methoxymethylpyrimidine (DE-A 4 116 089), 3.1 g (20 mmol) of 4-isobutylidene-cyclohexylamine and 3.0 g (30 mmol) of triethylamine were stirred for 3 hours without solvent at 80°–90° C. After cooling, the mixture was taken up in water/toluene, and the organic phase was dried and evaporated on a rotary evaporator. Purification by chromatography (silica gel/ethyl acetate) gave 2.2 g (36% of theory) of a virtually colorless oil.

Preparation of the starting material 4-isobutylidenecyclohexylamine 26.7 g (0.18 mol) of 4-isobutylidenecyclohexanone (prepared with isobutyltriphenylphosphonium bromide/sodium hydride and cyclohexane-1,4-dione monoethylene ketal in DMSO, followed by hydrolysis of the ketal) in 200 ml of ammonia-saturated methanol was subjected to reductive amination at 100° C. at a hydrogen pressure of 100 bar in the presence of 6 g of Raney nickel. After the catalyst had been removed by filtration and the methanol had been stripped off, the crude product was distilled on a thin-layer evaporator (135° C./0.6 bar). 16.5 g (61% of theory) of a pale yellow oil were obtained.

Example b 4-(4-hexylidene-cyclohexyloxy)-quinazoline

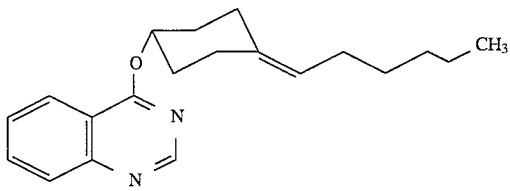

130 mg (4.3 mmol) of 80% NaH are added to a solution of 0.7 g (3.5 mmol) of 4-hexylidenecyclohexanol in 20 ml of absolute THF, and the mixture is refluxed for 1 hour until deproteination is complete. 0.6 g (3.6 mmol) of 4-chloro-quinazoline is subsequently added to the reaction solution at boiling point, and the mixture is refluxed for 3 hours. For working up, 2 ml of isopropanol are added. After cooling, the mixture is taken up in aqueous $NH_4Cl$/ether and the organic phase is dried over $MgSO_4$. Concentration of the solvent gives 1.1 g (crude product which is purified by flash chromatography (silica gel/petroleum ether:ethyl acetate= 2:1)).

Yield: 0.75 g (65% of theory) of pale yellow oil.

Example c

4-[4-(n-butoximino)cyclohexyloxy]-5,6,7,8-tetrahydroquinazoline

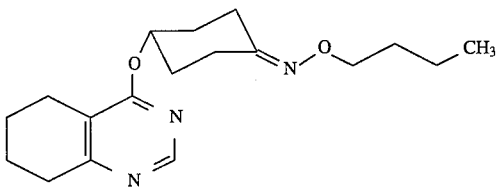

140 mg (4.6 mmol) of 80% sodium hydride are added to a solution of 1.13 g (3.8 mmol) of 4-[4-(hydroxylimino)-cyclohexyloxy]-5,6,7,8-tetrahydroquinazoline in 30 ml of absolute THF, and the mixture is stirred for approximately 15 minutes at room temperature until evolution of hydrogen can no longer be observed. 0.9 ml (8.2 mmol) of n-butyl bromide is added dropwise to the reaction solution, and the mixture is refluxed until the reaction is complete.

For working up, the mixture is cooled, 1–2 ml of isopropanol are then added, stirring is continued for a further 15 minutes, and the reaction mixture is poured into 50 ml of an aqueous ammoniumchloride solution. The aqueous phase is extracted using ether, and the combined organic phases are dried over $MgSO_4$. After concentration, 1.4 g of crude product remain, and these are purified by flash chromatography (silica gel, ethyl acetate).

Yield: 1.0 g (75% of theory) of pale yellow oil.

Preparation of the starting material 4-[4-(hydroxylimino) cyclohexyloxy]-5,6,7,8-tetrahydroquinazoline A solution of 3.8 g (15.5 mmol) of 4-(cyclohexanone-4-oxy)-5,6,7,8-tetrahydroquinazoline in 50 ml of distilled ethanol is first treated with 2.9 g (34.2 mmol) of sodium acetate and then with 2.2 g (31.0 mmol) of hydroxyl ammonium chloride. The reaction mixture is refluxed for 4 hours, and the crystallized product (1.8 g) is subsequently removed by filtration with suction.

The filtrate is concentrated, the concentrate is taken up in 50 ml of ethyl acetate, and the mixture is washed with dilute ammonium chloride solution. The aqueous phase is washed thoroughly using ethyl acetate, and the organic phase is dried over $MgSO_4$. After concentration, a further 1.2 g of pure product are obtained.

Yield: 3.0 g (65% of theory) of pale yellow crystals, m.p. 182° C.

Preparation of the starting material 4-(cyclohexanone-4-oxy)-5,6,7,8-tetrahydroquinazoline 1.20 g (40.0 mmol) of 80% NaH are added to a solution of 5.7 g (36.0 mmol) of 4-hydroxycyclohexanone ethylene ketal in 50 ml of absolute THF, and the mixture is refluxed for 1 hour. The reaction solution is then cooled to approximately 35° C., and 6.0 g (36.0 mmol) of 4-chloro-5,6,7,8-tetrahydroquinazoline, dissolved in 30 ml of THF, are added dropwise. The reaction solution is refluxed for a further 4 hours.

For working up, 10 ml of isopropanol are added dropwise, and the reaction mixture is poured into 2N of HCl and stirred until elimination of the protective group is complete. The mixture is then neutralized using $NaHCO_3$ solution, and the aqueous phase is extracted using $Et_2O$. The organic phase is dried over $MgSO_4$ and subsequently evaporated on a rotary evaporator. The residue (7.2 g) is purified by flash chromatography (silica gel, ethyl acetate).

Yield: 4.8 g (56% of theory) of colorless oil.

Preparation of the starting material 4-hydroxycyclohexanone ethylene ketal 3.6 g (95 mmol) of $NaBH_4$ are added to a solution of 50 g (25 mmol) of 1,4-cyclohexanedione monoethylene ketal and the mixture is stirred until the reaction is complete. For working up, 30 ml of acetone are added and stirring is continued for 30 minutes. The mixture is subsequently evaporated to dryness and the residue is taken up in 200 ml of ether, the organic phase is washed with aqueous $NH_4Cl$ solution and water, and the organic phase is dried over $MgSO_4$. The solvent is subsequently evaporated on a rotary evaporator and the residue is dried.

Yield: 46.0 g (91% of theory) of colorless oil

The compounds of Tables 2 to 6 were prepared analogously.

Meanings of substituents $T^n$ are defined in Table 1.

TABLE 1

$$T^n = -\left\langle \begin{array}{c}(CH_2)_n\\(CH_2)_m\end{array}\right\rangle = Y$$

| Radical/Example No. | m | n | R⁴ | Y |
|---|---|---|---|---|
| $T^1$ | 2 | 2 | H | $CH_2$ |
| $T^2$ | 2 | 2 | H | $CHCH_3$ |
| $T^3$ | 2 | 2 | H | $CHCH_2CH_3$ |
| $T^4$ | 2 | 2 | H | $CHCH_2CH_2CH_3$ |
| $T^5$ | 2 | 2 | H | $CHCH(CH_3)_2$ |
| $T^6$ | 2 | 2 | H | $CH(CH_2)_3CH_3$ |
| $T^7$ | 2 | 2 | H | $CHCH(CH_3)CH_2CH_3$ |
| $T^8$ | 2 | 2 | H | $CHCH_2CH(CH_3)_2$ |
| $T^9$ | 2 | 2 | H | $CHC(CH_3)_3$ |
| $T^{10}$ | 2 | 2 | H | $CH(CH_2)_4CH_3$ |
| $T^{11}$ | 2 | 2 | H | $CHCH(CH_3)CH_2CH_2CH_3$ |
| $T^{12}$ | 2 | 2 | H | $CHCH_2CH(CH_3)CH_2CH_3$ |
| $T^{13}$ | 2 | 2 | H | $CHCH_2CH_2CH(CH_3)CH_3$ |
| $T^{14}$ | 2 | 2 | H | $CHCH_2C(CH_3)_3$ |
| $T^{15}$ | 2 | 2 | H | $CH(CH_2)_5CH_3$ |
| $T^{16}$ | 2 | 2 | H | $CH(CH_2)_6CH_3$ |
| $T^{17}$ | 2 | 2 | H | $CHC(CH_3)_2CH_2CH(CH_3)_2$ |
| $T^{18}$ | 2 | 2 | H | $CH(CH_2)_7CH_3$ |
| $T^{19}$ | 2 | 2 | H | $CH(CH_3)_2CHC(CH_3)_3$ |
| $T^{20}$ | 2 | 2 | H | $C(CH_3)_2$ |
| $T^{21}$ | 2 | 2 | H | $C(CH_3)CH_2CH_3$ |
| $T^{22}$ | 2 | 2 | H | $C(CH_3)CH_2CH_2CH_3$ |
| $T^{23}$ | 2 | 2 | H | $C(CH_3)(CH_2)_3CH_3$ |
| $T^{24}$ | 2 | 2 | H | $C(CH_3)(CH_2)_5CH_3$ |
| $T^{25}$ | 2 | 2 | H | $C(CH_3)(CH_2)_7CH_3$ |
| $T^{26}$ | 2 | 2 | H | $C(CH_2CH_3)_2$ |
| $T^{27}$ | 2 | 2 | H | 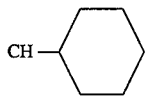 |
| $T^{28}$ | 2 | 2 | H | 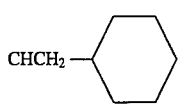 |
| $T^{29}$ | 2 | 2 | H | 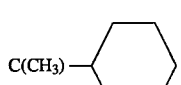 |
| $T^{30}$ | 2 | 2 | H | CHPhe |
| $T^{31}$ | 2 | 2 | H |  |
| $T^{32}$ | 2 | 2 | H | 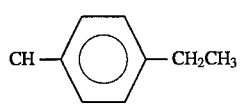 |
| $T^{33}$ | 2 | 2 | H | 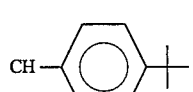 |
| $T^{34}$ | 2 | 2 | H |  |
| $T^{35}$ | 2 | 2 | H | 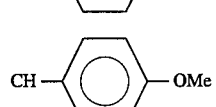 |

TABLE 1-continued $$T^n = -\begin{pmatrix} (CH_2)_n \\ (CH_2)_m \end{pmatrix} = Y$$

| Radical/Example No. | m | n | R⁴ | Y |
|---|---|---|---|---|
| T³⁶ | 2 | 2 | H | CH—⟨C₆H₄⟩—OCH₂CH₃ |
| T³⁷ | 2 | 2 | H | CH—⟨C₆H₄⟩—O—CF₃ |
| T³⁸ | 2 | 2 | H | CH—⟨C₆H₄⟩—COO—C(CH₃)₂ |
| T³⁹ | 2 | 2 | H | CH—⟨C₆H₄⟩—CF₃ |
| T⁴⁰ | 2 | 2 | H | CH—⟨C₆H₄⟩—O—CH₂CH₂—OCH₂CH₃ |
| T⁴¹ | 2 | 2 | H | C-cyclopropyl |
| T⁴² | 2 | 2 | H | C-cyclopentyl |
| T⁴³ | 2 | 2 | H | C-cyclohexyl |
| T⁴⁴ | 2 | 2 | H | CH—O—CH₃ |
| T⁴⁵ | 2 | 2 | H | CH—O—CH₂CH₃ |
| T⁴⁶ | 2 | 2 | H | CH—O—(CH₂)₃CH₃ |
| T⁴⁷ | 2 | 2 | H | CH—CH₂—O—CH₃ |
| T⁴⁸ | 2 | 2 | H | CH—CH₂—O—CH₂CH₃ |
| T⁴⁹ | 2 | 2 | H | CH—CH₂—O—(CH₂)₃CH₃ |
| T⁵⁰ | 2 | 2 | H | CH—CH₂—O—CH₂CH₂—O—CH₂—CH₃ |
| T⁵¹ | 2 | 2 | H | CH—CH₂—Si(CH₃)₃ |
| T⁵² | 2 | 2 | H | CHCOOCH₂CH₃ |
| T⁵³ | 2 | 2 | H | CHCO—⟨C₆H₅⟩ |
| T⁵⁴ | 2 | 2 | H | C(⟨C₆H₅⟩)(⟨C₆H₅⟩) |

TABLE 1-continued $$T^n = \underset{(CH_2)_m}{\overset{(CH_2)_n}{-\!\!\!\!<\!\!\!\!\!>\!\!=\!Y}}$$

| Radical/Example No. | m | n | $R^4$ | Y |
|---|---|---|---|---|
| $T^{55}$ | 2 | 2 | H | 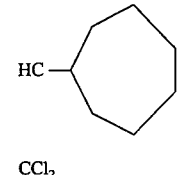 HC—(cycloheptyl) |
| $T^{56}$ | 2 | 2 | H | $CCl_2$ |
| $T^{57}$ | 3 | 2 | H | $CH(CH_2)_2CH_3$ |
| $T^{58}$ | 1 | 2 | H | $CH(CH_2)_2CH_3$ |
| $T^{59}$ | 1 | 1 | H | $CH(CH_2)_2CH_3$ |
| $T^{60}$ | 0 | 1 | H | $CH(CH_2)_2CH_3$ |
| $T^{61}$ | 2 | 2 | H | $N-O-H$ |
| $T^{62}$ | 2 | 2 | H | $N-O-CH_2CH_3$ |
| $T^{63}$ | 2 | 2 | H | $N-O-(CH_2)_2CH_3$ |
| $T^{64}$ | 2 | 2 | H | $N-O-CH(CH_3)_2$ |
| $T^{65}$ | 2 | 2 | H | $N-O-(CH_2)_3CH_3$ |
| $T^{66}$ | 2 | 2 | H | $N-O-CH(CH_3)CH_2CH_3$ |
| $T^{67}$ | 2 | 2 | H | $N-O-CH_2-CH(CH_3)_2$ |
| $T^{68}$ | 2 | 2 | H | $N-O-C(CH_3)_3$ |
| $T^{69}$ | 2 | 2 | H | $N-O-(CH_2)_4CH_3$ |
| $T^{70}$ | 2 | 2 | H | $N-O-CH(CH_3)(CH_2)_2CH_3$ |
| $T^{71}$ | 2 | 2 | H | $N-O-(CH_2)_2CH(CH_3)_2$ |
| $T^{72}$ | 2 | 2 | H | $N-O-CH_2-C(CH_3)_3$ |
| $T^{73}$ | 2 | 2 | H | $N-O-(CH_2)_5CH_3$ |
| $T^{74}$ | 2 | 2 | H | $N-O-CH(CH_3)(CH_2)_3CH_3$ |
| $T^{75}$ | 2 | 2 | H | $N-O-(CH_2)_6CH_3$ |
| $T^{76}$ | 2 | 2 | H | $N-O-(CH_2)_7CH_3$ |
| $T^{77}$ | 2 | 2 | H | 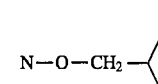 N—O—(cyclohexyl) |
| $T^{78}$ | 2 | 2 | H | 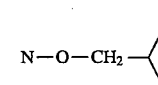 N—O—CH$_2$—(cyclopentyl) |
| $T^{79}$ | 2 | 2 | H | 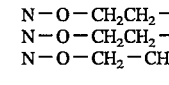 N—O—CH$_2$—(cyclohexyl) |
| $T^{80}$ | 2 | 2 | H | $N-O-CH_2CH_2-O-CH_2CH_3$ |
| $T^{81}$ | 2 | 2 | H | $N-O-CH_2CH_2-O-(CH_2)_3CH_3$ |
| $T^{82}$ | 2 | 2 | H | $N-O-CH_2-CH_2-O-CH_2CH_2OCH_2CH_3$ |
| $T^{83}$ | 2 | 2 | H | 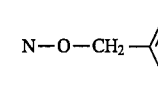 N—O—(phenyl) |
| $T^{84}$ | 2 | 2 | H | 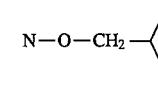 N—O—CH$_2$—(phenyl) |
| $T^{85}$ | 2 | 2 | H | 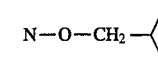 N—O—CH$_2$—(phenyl)—Cl |
| $T^{86}$ | 2 | 2 | H |  N—O—CH$_2$—(phenyl)—C(CH$_3$)$_3$ |

TABLE 1-continued $$T^n = -\left\langle\begin{array}{c}(CH_2)_n\\(CH_2)_m\end{array}\right\rangle = Y$$

| Radical/Example No. | m | n | $R^4$ | Y |
|---|---|---|---|---|
| $T^{87}$ | 2 | 2 | H | $N-O-CF_2CFH-O-CF_2-CF_2CF_2H$ |
| $T^{88}$ | 2 | 2 | H | $N-O-CF_2CFH-O-CF_2CF_2CF_2$ |
| $T^{89}$ | 2 | 2 | H | $N-O-CO-CH_3$ |
| $T^{90}$ | 2 | 2 | H | $N-O-CO-(CH_2)_3CH_3$ |
| $T^{91}$ | 2 | 2 | H | $N-O-CO-C(CH_3)_3$ |
| $T^{92}$ | 2 | 2 | H | 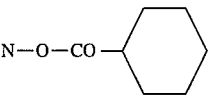 |
| $T^{93}$ | 2 | 2 | H | 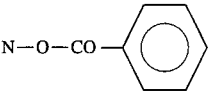 |
| $T^{94}$ | 2 | 2 | H | 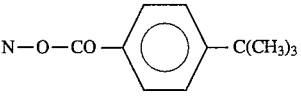 |
| $T^{95}$ | 2 | 2 | H | 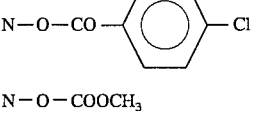 |
| $T^{96}$ | 2 | 2 | H | $N-O-COOCH_3$ |
| $T^{97}$ | 2 | 2 | H | $N-O-COOC(CH_3)_3$ |
| $T^{98}$ | 2 | 2 | H | 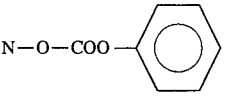 |
| $T^{99}$ | 2 | 2 | H | $N-O-CH_2-COO-CH_2CH_3$ |
| $T^{100}$ | 2 | 2 | H | 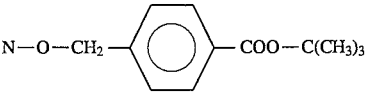 |
| $T^{101}$ | 2 | 2 | H | $N-O-CH_2COOCH_2CH_3$ |
| $T^{102}$ | 2 | 2 | H | 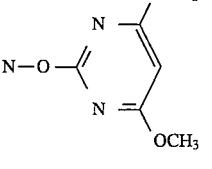 |
| $T^{103}$ | 2 | 2 | H | 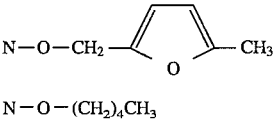 |
| $T^{104}$ | 3 | 2 | H | $N-O-(CH_2)_4CH_3$ |
| $T^{105}$ | 1 | 2 | H | $N-O-(CH_2)_4CH_3$ |
| $T^{106}$ | 0 | 1 | H | $N-O-(CH_2)_4CH_3$ |
| $T^{107}$ | 2 | 2 | H | $N-(CH_2)_3CH_3$ |
| $T^{108}$ | 2 | 2 | H |  |

TABLE 1-continued $$T^n = \left\langle \begin{array}{c}(CH_2)_n\\(CH_2)_m\end{array}\right\rangle = Y$$

| Radical/Example No. | m | n | R⁴ | Y |
|---|---|---|---|---|
| $T^{109}$ | 2 | 2 | H | 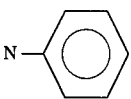 |
| $T^{110}$ | 2 | 2 | H | 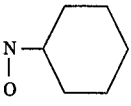 |
| $T^{111}$ | 2 | 2 | H | 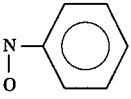 |
| $T^{112}$ | 2 | 2 | H | 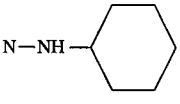 |
| $T^{113}$ | 2 | 2 | H | N—NH—C(CH₃)₃ |
| $T^{114}$ | 2 | 2 | H | 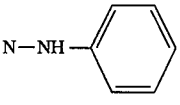 |
| $T^{115}$ | 2 | 2 | H | 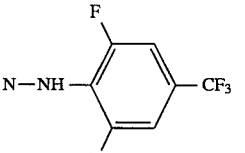 |
| $T^{116}$ | 2 | 2 | H | 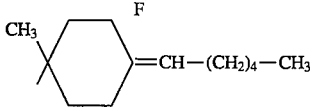 |
| $T^{117}$ | | | | 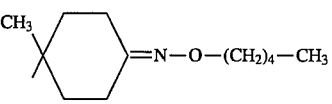 |
| $T^{118}$ | | | | (see image above) |

TABLE 2

$$\begin{array}{c}X-T^n\\R^3\diagdown\diagup A\\R^2\diagdown N\diagup R^1\end{array}$$

| Example No. | A | X | R¹ | R² | R³ | Tⁿ | m.p. [°C.] |
|---|---|---|---|---|---|---|---|
| 1 | N | O | H | CH₃CH₂ | Cl | $T^2$ | |
| 2 | N | NH | H | CH₃CH₂ | Cl | $T^2$ | |
| 3 | N | O | H | CH₃OCH₂ | CH₃O | $T^2$ | |
| 4 | N | NH | H | CH₃OCH₂ | CH₃O | $T^2$ | |
| 5 | N | O | H | CH₃CH₂ | Cl | $T^4$ | |
| 6 | N | NH | H | CH₃CH₂ | Cl | $T^4$ | |
| 7 | N | O | H | CH₃OCH₂ | CH₃O | $T^4$ | |
| 8 | N | NH | H | CH₃OCH₂ | CH₃O | $T^4$ | |

TABLE 2-continued $$\begin{array}{c} R^3 \\ | \\ R^2 \end{array} \underset{N}{\overset{X-T^n}{\underset{|}{\bigvee}}} \overset{A}{\underset{R^1}{\bigvee}}$$

| Example No. | A | X | $R^1$ | $R^2$ | $R^3$ | $T^n$ | m.p. [°C.] |
|---|---|---|---|---|---|---|---|
| 9 | N | O | H | $CH_3CH_2$ | Cl | $T^5$ | |
| 10 | N | NH | H | $CH_3CH_2$ | Cl | $T^5$ | |
| 11 | N | O | H | $CH_3OCH_2$ | $CH_3O$ | $T^5$ | |
| 12 | N | NH | H | $CH_3OCH_2$ | $CH_3O$ | $T^5$ | |
| 13 | N | O | H | $CH_3CH_2$ | Cl | $T^9$ | |
| 14 | N | NH | H | $CH_3CH_2$ | Cl | $T^9$ | |
| 15 | N | O | H | $CH_3OCH_2$ | $CH_3O$ | $T^9$ | |
| 16 | N | NH | H | $CH_3OCH_2$ | $CH_3O$ | $T^9$ | |
| 17 | N | O | H | $CH_3CH_2$ | Cl | $T^{10}$ | oil |
| 18 | N | NH | H | $CH_3CH_2$ | Cl | $T^{10}$ | oil |
| 19 | N | O | H | $CH_3OCH_2$ | $CH_3O$ | $T^{10}$ | oil |
| 20 | N | NH | H | $CH_3OCH_2$ | $CH_3O$ | $T^{10}$ | |
| 21 | N | O | H | $CH_3CH_2$ | Cl | $T^{16}$ | |
| 22 | N | NH | H | $CH_3CH_2$ | Cl | $T^{16}$ | |
| 23 | N | O | H | $CH_3OCH_2$ | $CH_3O$ | $T^{16}$ | |
| 24 | N | NH | H | $CH_3OCH_2$ | $CH_3O$ | $T^{16}$ | |
| 25 | N | O | H | $CH_3CH_2$ | Cl | $T^{21}$ | |
| 26 | N | NH | H | $CH_3CH_2$ | Cl | $T^{21}$ | |
| 27 | N | O | H | $CH_3OCH_2$ | $CH_3O$ | $T^{21}$ | |
| 28 | N | NH | H | $CH_3OCH_2$ | $CH_3O$ | $T^{21}$ | |
| 29 | N | O | H | $CH_3CH_2$ | Cl | $T^{27}$ | |
| 30 | N | NH | H | $CH_3CH_2$ | Cl | $T^{27}$ | |
| 31 | N | O | H | $CH_3OCH_2$ | $CH_3O$ | $T^{27}$ | |
| 32 | N | NH | H | $CH_3OCH_2$ | $CH_3O$ | $T^{27}$ | |
| 33 | N | O | H | $CH_3CH_2$ | Cl | $T^{36}$ | |
| 34 | N | NH | H | $CH_3CH_2$ | Cl | $T^{36}$ | 79–81 |
| 35 | N | O | H | $CH_3OCH_2$ | $CH_3O$ | $T^{36}$ | oil |
| 36 | N | NH | H | $CH_3OCH_2$ | $CH_3O$ | $T^{36}$ | |
| 37 | N | O | H | $CH_3CH_2$ | Cl | $T^{38}$ | |
| 38 | N | NH | H | $CH_3CH_2$ | Cl | $T^{38}$ | |
| 39 | N | O | H | $CH_3OCH_2$ | $CH_3$ | $T^{38}$ | |
| 40 | N | NH | H | $CH_3OCH_2$ | $CH_3$ | $T^{38}$ | |
| 41 | N | O | H | $CH_3CH_2$ | Cl | $T^{40}$ | |
| 42 | N | NH | H | $CH_3CH_2$ | Cl | $T^{40}$ | |
| 43 | N | O | H | $CH_3OCH_2$ | $CH_3O$ | $T^{40}$ | |
| 44 | N | NH | H | $CH_3OCH_2$ | $CH_3O$ | $T^{40}$ | |
| 45 | N | O | H | $CH_3CH_2$ | Cl | $T^{43}$ | |
| 46 | N | NH | H | $CH_3CH_2$ | Cl | $T^{43}$ | |
| 47 | N | O | H | $CH_3OCH_2$ | $CH_3O$ | $T^{43}$ | |
| 48 | N | NH | H | $CH_3OCH_2$ | $CH_3O$ | $T^{43}$ | |
| 49 | N | O | H | $CH_3CH_2$ | Cl | $T^{44}$ | |
| 50 | N | NH | H | $CH_3CH_2$ | Cl | $T^{44}$ | |
| 51 | N | O | H | $CH_3OCH_2$ | $CH_3O$ | $T^{44}$ | |
| 52 | N | NH | H | $CH_3OCH_2$ | $CH_3O$ | $T^{44}$ | |
| 53 | N | O | H | $CH_3CH_2$ | Cl | $T^{48}$ | |
| 54 | N | NH | H | $CH_3CH_2$ | Cl | $T^{48}$ | |
| 55 | N | O | H | $CH_3OCH_2$ | $CH_3$ | $T^{48}$ | |
| 56 | N | NH | H | $CH_3OCH_2$ | $CH_3O$ | $T^{48}$ | |
| 57 | N | O | H | $CH_3CH_2$ | Cl | $T^{52}$ | |
| 58 | N | NH | H | $CH_3CH_2$ | Cl | $T^{52}$ | |
| 59 | N | O | H | $CH_3OCH_2$ | $CH_3O$ | $T^{52}$ | |
| 60 | N | NH | H | $CH_3OCH_2$ | $CH_3O$ | $T^{52}$ | |
| 61 | N | O | H | $CH_3CH_2$ | Cl | $T^{61}$ | |
| 62 | N | NH | H | $CH_3CH_2$ | Cl | $T^{61}$ | |
| 63 | N | O | H | $CH_3OCH_2$ | $CH_3$ | $T^{61}$ | |
| 64 | N | NH | H | $CH_3OCH_2$ | $CH_3O$ | $T^{61}$ | |
| 65 | N | O | H | $CH_3CH_2$ | Cl | $T^{62}$ | |
| 66 | N | NH | H | $CH_3CH_2$ | Cl | $T^{62}$ | |
| 67 | N | O | H | $CH_3OCH_2$ | $CH_3O$ | $T^{62}$ | |
| 68 | N | NH | H | $CH_3OCH_2$ | $CH_3O$ | $T^{62}$ | |
| 69 | N | O | H | $CH_3CH_2$ | Cl | $T^{65}$ | oil |
| 70 | N | NH | H | $CH_3CH_2$ | Cl | $T^{65}$ | |
| 71 | N | O | H | $CH_3OCH_2$ | $CH_3O$ | $T^{65}$ | oil |
| 72 | N | NH | H | $CH_3OCH_2$ | $CH_3$ | $T^{65}$ | |
| 72a | N | O | H | $CH_3CH_2$ | Cl | $T^{68}$ | 48–51 |
| 73 | N | O | H | $CH_3CH_2$ | Cl | $T^{69}$ | |
| 74 | N | NH | H | $CH_3CH_2$ | Cl | $T^{69}$ | |
| 75 | N | O | H | $CH_3OCH_2$ | $CH_3O$ | $T^{69}$ | |
| 76 | N | NH | H | $CH_3OCH_2$ | $CH_3O$ | $T^{69}$ | |
| 77 | N | O | H | $CH_3CH_2$ | Cl | $T^{73}$ | |
| 78 | N | NH | H | $CH_3CH_2$ | Cl | $T^{73}$ | |
| 79 | N | O | H | $CH_3OCH_2$ | $CH_3O$ | $T^{73}$ | |
| 80 | N | NH | H | $CH_3OCH_2$ | $CH_3O$ | $T^{73}$ | |
| 81 | N | O | H | $CH_3CH_2$ | Cl | $T^{76}$ | |
| 82 | N | NH | H | $CH_3CH_2$ | Cl | $T^{76}$ | |
| 82a | N | O | H | $CH_3OCH_2$ | $CH_3O$ | $T^{68}$ | oil |
| 83 | N | O | H | $CH_3OCH_2$ | $CH_3O$ | $T^{76}$ | |
| 84 | N | NH | H | $CH_3OCH_2$ | $CH_3O$ | $T^{76}$ | |
| 85 | N | O | H | $CH_3CH_2$ | Cl | $T^{79}$ | |
| 86 | N | NH | H | $CH_3CH_2$ | Cl | $T^{79}$ | |
| 87 | N | O | H | $CH_3OCH_2$ | $CH_3O$ | $T^{79}$ | |
| 88 | N | NH | H | $CH_3OCH_2$ | $CH_3O$ | $T^{79}$ | |
| 89 | N | O | H | $CH_3CH_2$ | Cl | $T^{81}$ | |
| 90 | N | NH | H | $CH_3CH_2$ | Cl | $T^{81}$ | |
| 91 | N | O | J | $CH_3OCH_2$ | $CH_3O$ | $T^{81}$ | |
| 92 | N | NH | H | $CH_3OCH_2$ | $CH_3O$ | $T^{81}$ | |
| 93 | N | O | H | $CH_3CH_2$ | Cl | $T^{82}$ | |
| 94 | N | NH | H | $CH_3CH_2$ | Cl | $T^{82}$ | |
| 95 | N | O | H | $CH_3OCH_2$ | $CH_3O$ | $T^{82}$ | |
| 96 | N | NH | H | $CH_3OCH_2$ | $CH_3O$ | $T^{82}$ | |
| 96a | N | O | H | $CH_3OCH_2$ | $CH_3O$ | $T^{83}$ | oil |
| 97 | N | O | H | $CH_3CH_2$ | Cl | $T^{84}$ | oil |
| 98 | N | NH | H | $CH_3CH_2$ | Cl | $T^{84}$ | |
| 99 | N | O | H | $CH_3OCH_2$ | $CH_3O$ | $T^{84}$ | oil |
| 100 | N | NH | H | $CH_3OCH_2$ | $CH_3O$ | $T^{84}$ | |
| 101 | N | O | H | $CH_3CH_2$ | Cl | $T^{87}$ | oil |
| 102 | N | NH | H | $CH_3CH_2$ | Cl | $T^{87}$ | |
| 103 | N | O | H | $CH_3OCH_2$ | $CH_3O$ | $T^{87}$ | oil |
| 104 | N | NH | H | $CH_3OCH_2$ | $CH_3O$ | $T^{87}$ | |
| 105 | N | O | H | $CH_3CH_2$ | Cl | $T^{89}$ | oil |
| 106 | N | NH | H | $CH_3CH_2$ | Cl | $T^{89}$ | |
| 107 | N | O | H | $CH_3OCH_2$ | $CH_3O$ | $T^{89}$ | |
| 108 | N | NH | H | $CH_3OCH_2$ | $CH_3O$ | $T^{89}$ | |
| 109 | N | O | H | $CH_3CH_2$ | Cl | $T^{91}$ | |
| 110 | N | NH | H | $CH_3CH_2$ | Cl | $T^{91}$ | |
| 111 | N | O | H | $CH_3OCH_2$ | $CH_3O$ | $T^{91}$ | |
| 112 | N | NH | H | $CH_3OCH_2$ | $CH_3O$ | $T^{91}$ | |
| 113 | N | O | H | $CH_3CH_2$ | Cl | $T^{94}$ | |
| 114 | N | NH | H | $CH_3CH_2$ | Cl | $T^{94}$ | |
| 115 | N | O | H | $CH_3OCH_2$ | $CH_3O$ | $T^{94}$ | |
| 116 | N | NH | H | $CH_3OCH_2$ | $CH_3O$ | $T^{94}$ | |
| 117 | N | O | H | $CH_3CH_2$ | Cl | $T^{100}$ | |
| 118 | N | NH | H | $CH_3CH_2$ | Cl | $T^{100}$ | |
| 119 | N | O | H | $CH_3OCH_2$ | $CH_3O$ | $T^{100}$ | |
| 120 | N | NH | H | $CH_3OCH_2$ | $CH_3O$ | $T^{100}$ | |
| 121 | N | O | H | $CH_3CH_2$ | Cl | $T^{118}$ | |
| 122 | N | NH | H | $CH_3CH_2$ | Cl | $T^{118}$ | |
| 123 | N | O | H | $CH_3OCH_2$ | $CH_3O$ | $T^{118}$ | |
| 124 | N | NH | H | $CH_3OCH_2$ | $CH_3O$ | $T^{118}$ | |
| 125 | N | O | H | $CH_3CH_2$ | Cl | $T^{30}$ | |
| 126 | N | NH | H | $CH_3CH_2$ | Cl | $T^{30}$ | oil |
| 127 | N | O | H | $CH_3OCH_2$ | $CH_3O$ | $T^{30}$ | |
| 128 | N | NH | H | $CH_3OCH_2$ | $CH_3O$ | $T^{30}$ | |

TABLE 3

![structure: X-T^n attached to ring with B, D, E, G, A, N, R^1]

| Example No. | A | B | D | E | G | X | R¹ | T^n | m.p. [°C.] |
|---|---|---|---|---|---|---|---|---|---|
| 129 | N | CH₂ | CH₂ | CH₂ | CH₂ | O | H | $T^2$ | |
| 130 | N | CH₂ | CH₂ | CH₂ | CH₂ | NH | H | $T^2$ | |
| 131 | N | CH | CH | CH | CH | O | H | $T^2$ | |
| 132 | N | CH | CH | CH | CH | NH | H | $T^2$ | |
| 133 | N | CH₂ | CH₂ | CH₂ | CH₂ | O | H | $T^4$ | |
| 134 | N | CH₂ | CH₂ | CH₂ | CH₂ | NH | H | $T^4$ | |
| 135 | N | CH | CH | CH | CH | O | H | $T^4$ | |
| 136 | N | CH | CH | CH | CH | NH | H | $T^4$ | |
| 137 | N | CH₂ | CH₂ | CH₂ | CH₂ | O | H | $T^9$ | |
| 138 | N | CH₂ | CH₂ | CH₂ | CH₂ | NH | H | $T^9$ | |
| 139 | N | CH | CH | CH | CH | O | H | $T^9$ | |
| 140 | N | CH | CH | CH | CH | NH | H | $T^9$ | |
| 141 | N | CH₂ | CH₂ | CH₂ | CH₂ | O | H | $T^{10}$ | oil |
| 142 | N | CH₂ | CH₂ | CH₂ | CH₂ | NH | H | $T^{10}$ | |
| 143 | N | CH | CH | CH | CH | O | H | $T^{10}$ | oil |
| 144 | N | CH | CH | CH | CH | NH | H | $T^{10}$ | |
| 145 | N | CH₂ | CH₂ | CH₂ | CH₂ | O | H | $T^{16}$ | |
| 146 | N | CH₂ | CH₂ | CH₂ | CH₂ | NH | H | $T^{16}$ | |
| 147 | N | CH | CH | CH | CH | O | H | $T^{16}$ | |
| 148 | N | CH | CH | CH | CH | NH | H | $T^{16}$ | |
| 149 | N | CH₂ | CH₂ | CH₂ | CH₂ | O | H | $T^{21}$ | |
| 150 | N | CH₂ | CH₂ | CH₂ | CH₂ | NH | H | $T^{21}$ | |
| 151 | N | CH | CH | CH | CH | O | H | $T^{21}$ | |
| 152 | N | CH | CH | CH | CH | NH | H | $T^{21}$ | |
| 153 | N | CH₂ | CH₂ | CH₂ | CH₂ | O | H | $T^{27}$ | |
| 154 | N | CH₂ | CH₂ | CH₂ | CH₂ | NH | H | $T^{27}$ | |
| 155 | N | CH | CH | CH | CH | O | H | $T^{27}$ | |
| 156 | N | CH | CH | CH | CH | NH | H | $T^{27}$ | |
| 157 | N | CH₂ | CH₂ | CH₂ | CH₂ | O | H | $T^{30}$ | |
| 158 | N | CH₂ | CH₂ | CH₂ | CH₂ | NH | H | $T^{30}$ | |
| 159 | N | CH | CH | CH | CH | O | H | $T^{30}$ | |
| 160 | N | CH | CH | CH | CH | NH | H | $T^{30}$ | |
| 161 | N | CH₂ | CH₂ | CH₂ | CH₂ | O | H | $T^{36}$ | 86–88 |
| 162 | N | CH₂ | CH₂ | CH₂ | CH₂ | NH | H | $T^{36}$ | |
| 163 | N | CH | CH | CH | CH | O | H | $T^{36}$ | oil |
| 164 | N | CH | CH | CH | CH | NH | H | $T^{36}$ | |
| 165 | N | CH₂ | CH₂ | CH₂ | CH₂ | O | H | $T^{38}$ | |
| 166 | N | CH₂ | CH₂ | CH₂ | CH₂ | NH | H | $T^{38}$ | |
| 167 | N | CH | CH | CH | CH | O | H | $T^{38}$ | |
| 168 | N | CH | CH | CH | CH | NH | H | $T^{38}$ | |
| 169 | N | CH₂ | CH₂ | CH₂ | CH₂ | O | H | $T^{40}$ | |
| 170 | N | CH₂ | CH₂ | CH₂ | CH₂ | NH | H | $T^{40}$ | |
| 171 | N | CH | CH | CH | CH | O | H | $T^{40}$ | |
| 172 | N | CH | CH | CH | CH | NH | H | $T^{40}$ | |
| 173 | N | CH₂ | CH₂ | CH₂ | CH₂ | O | H | $T^{43}$ | |
| 174 | N | CH₂ | CH₂ | CH₂ | CH₂ | NH | H | $T^{43}$ | |
| 175 | N | CH | CH | CH | CH | O | H | $T^{43}$ | |
| 176 | N | CH | CH | CH | CH | NH | H | $T^{43}$ | |
| 177 | N | CH₂ | CH₂ | CH₂ | CH₂ | O | H | $T^{44}$ | |
| 178 | N | CH₂ | CH₂ | CH₂ | CH₂ | NH | H | $T^{44}$ | |
| 179 | N | CH | CH | CH | CH | O | H | $T^{44}$ | |
| 180 | N | CH | CH | CH | CH | NH | H | $T^{44}$ | |
| 181 | N | CH₂ | CH₂ | CH₂ | CH₂ | O | H | $T^{48}$ | |
| 182 | N | CH₂ | CH₂ | CH₂ | CH₂ | NH | H | $T^{48}$ | |
| 183 | N | CH | CH | CH | CH | O | H | $T^{48}$ | |
| 184 | N | CH | CH | CH | CH | NH | H | $T^{48}$ | |
| 185 | N | CH₂ | CH₂ | CH₂ | CH₂ | O | H | $T^{52}$ | |
| 186 | N | CH₂ | CH₂ | CH₂ | CH₂ | NH | H | $T^{52}$ | |
| 187 | N | CH | CH | CH | CH | O | H | $T^{52}$ | |
| 188 | N | CH | CH | CH | CH | NH | H | $T^{52}$ | |
| 189 | N | CH₂ | CH₂ | CH₂ | CH₂ | O | H | $T^{61}$ | 182 |
| 190 | N | CH₂ | CH₂ | CH₂ | CH₂ | NH | H | $T^{61}$ | |
| 191 | N | CH | CH | CH | CH | O | H | $T^{61}$ | |
| 192 | N | CH | CH | CH | CH | NH | H | $T^{61}$ | |
| 193 | N | CH₂ | CH₂ | CH₂ | CH₂ | O | H | $T^{62}$ | oil |
| 194 | N | CH₂ | CH₂ | CH₂ | CH₂ | NH | H | $T^{62}$ | |
| 195 | N | CH | CH | CH | CH | O | H | $T^{62}$ | |
| 196 | N | CH | CH | CH | CH | NH | H | $T^{62}$ | |
| 197 | N | CH₂ | CH₂ | CH₂ | CH₂ | O | H | $T^{65}$ | oil |
| 198 | N | CH₂ | CH₂ | CH₂ | CH₂ | NH | H | $T^{65}$ | |
| 199 | N | CH | CH | CH | CH | O | H | $T^{65}$ | |
| 200 | N | CH | CH | CH | CH | NH | H | $T^{65}$ | |
| 200a | N | CH | CH | CH | CH | O | H | $T^{68}$ | 98–99 |
| 200b | N | CH₂ | CH₂ | CH₂ | CH₂ | O | H | $T^{68}$ | 81–83 |
| 201 | N | CH₂ | CH₂ | CH₂ | CH₂ | O | H | $T^{69}$ | oil |
| 202 | N | CH₂ | CH₂ | CH₂ | CH₂ | NH | H | $T^{69}$ | |
| 203 | N | CH | CH | CH | CH | O | H | $T^{69}$ | |
| 204 | N | CH | CH | CH | CH | NH | H | $T^{69}$ | |
| 205 | N | CH₂ | CH₂ | CH₂ | CH₂ | O | H | $T^{73}$ | |
| 206 | N | CH₂ | CH₂ | CH₂ | CH₂ | NH | H | $T^{73}$ | |
| 207 | N | CH | CH | CH | CH | O | H | $T^{73}$ | |
| 208 | N | CH | CH | CH | CH | NH | H | $T^{73}$ | |
| 209 | N | CH₂ | CH₂ | CH₂ | CH₂ | O | H | $T^{76}$ | |
| 210 | N | CH₂ | CH₂ | CH₂ | CH₂ | NH | H | $T^{76}$ | |
| 211 | N | CH | CH | CH | CH | O | H | $T^{76}$ | |
| 212 | N | CH | CH | CH | CH | NH | H | $T^{76}$ | |
| 213 | N | CH₂ | CH₂ | CH₂ | CH₂ | O | H | $T^{79}$ | |
| 214 | N | CH₂ | CH₂ | CH₂ | CH₂ | NH | H | $T^{79}$ | |
| 215 | N | CH | CH | CH | CH | O | H | $T^{79}$ | |
| 216 | N | CH | CH | CH | CH | NH | H | $T^{79}$ | |
| 217 | N | CH₂ | CH₂ | CH₂ | CH₂ | O | H | $T^{81}$ | oil |
| 218 | N | CH₂ | CH₂ | CH₂ | CH₂ | NH | H | $T^{81}$ | |
| 219 | N | CH | CH | CH | CH | O | H | $T^{81}$ | |
| 220 | N | CH | CH | CH | CH | NH | H | $T^{81}$ | |
| 221 | N | CH₂ | CH₂ | CH₂ | CH₂ | O | H | $T^{82}$ | oil |
| 222 | N | CH₂ | CH₂ | CH₂ | CH₂ | NH | H | $T^{82}$ | |
| 223 | N | CH | CH | CH | CH | O | H | $T^{82}$ | |
| 224 | N | CH | CH | CH | CH | NH | H | $T^{82}$ | |
| 224a | N | CH₂ | CH₂ | CH₂ | CH₂ | O | H | $T^{83}$ | oil |
| 225 | N | CH₂ | CH₂ | CH₂ | CH₂ | O | H | $T^{84}$ | oil |
| 226 | N | CH₂ | CH₂ | CH₂ | CH₂ | NH | H | $T^{84}$ | |
| 227 | N | CH | CH | CH | CH | O | H | $T^{84}$ | |
| 228 | N | CH | CH | CH | CH | NH | H | $T^{84}$ | |
| 229 | N | CH₂ | CH₂ | CH₂ | CH₂ | O | H | $T^{87}$ | oil |
| 230 | N | CH₂ | CH₂ | CH₂ | CH₂ | NH | H | $T^{87}$ | |
| 231 | N | CH | CH | CH | CH | O | H | $T^{87}$ | |
| 232 | N | CH | CH | CH | CH | NH | H | $T^{87}$ | |
| 233 | N | CH₂ | CH₂ | CH₂ | CH₂ | O | H | $T^{89}$ | |
| 234 | N | CH₂ | CH₂ | CH₂ | CH₂ | NH | H | $T^{89}$ | |
| 235 | N | CH | CH | CH | CH | O | H | $T^{89}$ | |
| 236 | N | CH | CH | CH | CH | NH | H | $T^{89}$ | |
| 237 | N | CH₂ | CH₂ | CH₂ | CH₂ | O | H | $T^{91}$ | |
| 238 | N | CH₂ | CH₂ | CH₂ | CH₂ | NH | H | $T^{91}$ | |
| 239 | N | CH | CH | CH | CH | O | H | $T^{91}$ | |
| 240 | N | CH | CH | CH | CH | NH | H | $T^{91}$ | |
| 241 | N | CH₂ | CH₂ | CH₂ | CH₂ | O | H | $T^{94}$ | |
| 242 | N | CH₂ | CH₂ | CH₂ | CH₂ | NH | H | $T^{94}$ | |
| 243 | N | CH | CH | CH | CH | O | H | $T^{94}$ | |
| 244 | N | CH | CH | CH | CH | NH | H | $T^{94}$ | |
| 245 | N | CH₂ | CH₂ | CH₂ | CH₂ | O | H | $T^{100}$ | |
| 246 | N | CH₂ | CH₂ | CH₂ | CH₂ | NH | H | $T^{100}$ | |
| 247 | N | CH | CH | CH | CH | O | H | $T^{100}$ | |
| 248 | N | CH | CH | CH | CH | NH | H | $T^{100}$ | |

TABLE 4

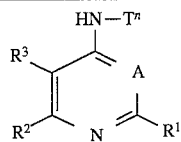

| Example No. | A | B | D | E | G | X | R¹ | Tⁿ | m.p. [°C.] |
|---|---|---|---|---|---|---|---|---|---|
| 249 | N | NH | | H | CH₃CH₂ | Cl | | T¹ | |
| 250 | N | NH | | H | CH₃CH₂ | Cl | | T³ | |
| 251 | N | NH | | H | CH₃CH₂ | Cl | | T⁷ | |
| 252 | N | NH | | H | CH₃CH₂ | Cl | | T⁸ | |
| 253 | N | NH | | H | CH₃CH₂ | Cl | | T¹¹ | |
| 254 | N | NH | | H | CH₃CH₂ | Cl | | T¹² | |
| 255 | N | NH | | H | CH₃CH₂ | Cl | | T¹³ | |
| 256 | N | NH | | H | CH₃CH₂ | Cl | | T¹⁴ | oil |
| 257 | N | NH | | H | CH₃CH₂ | Cl | | T¹⁵ | |
| 258 | N | NH | | H | CH₃CH₂ | Cl | | T¹⁷ | |
| 259 | N | NH | | H | CH₃CH₂ | Cl | | T¹⁸ | oil |
| 260 | N | NH | | H | CH₃CH₂ | Cl | | T¹⁹ | |
| 261 | N | NH | | H | CH₃CH₂ | Cl | | T²⁰ | |
| 262 | N | NH | | H | CH₃CH₂ | Cl | | T²² | |
| 263 | N | NH | | H | CH₃CH₂ | Cl | | T²³ | |
| 264 | N | NH | | H | CH₃CH₂ | Cl | | T²⁴ | |
| 265 | N | NH | | H | CH₃CH₂ | Cl | | T²⁵ | |
| 266 | N | NH | | H | CH₃CH₂ | Cl | | T²⁶ | |
| 267 | N | NH | | H | CH₃CH₂ | Cl | | T²⁸ | |
| 268 | N | NH | | H | CH₃CH₂ | Cl | | T²⁹ | |
| 269 | N | NH | | H | CH₃CH₂ | Cl | | T³¹ | |
| 270 | N | NH | | H | CH₃CH₂ | Cl | | T³² | |
| 271 | N | NH | | H | CH₃CH₂ | Cl | | T³³ | |
| 272 | N | NH | | H | CH₃CH₂ | Cl | | T³⁴ | |
| 273 | N | NH | | H | CH₃CH₂ | Cl | | T³⁵ | |
| 274 | N | NH | | H | CH₃CH₂ | Cl | | T³⁷ | |
| 275 | N | NH | | H | CH₃CH₂ | Cl | | T³⁹ | |
| 276 | N | NH | | H | CH₃CH₂ | Cl | | T⁴¹ | |
| 277 | N | NH | | H | CH₃CH₂ | Cl | | T⁴² | |
| 278 | N | NH | | H | CH₃CH₂ | Cl | | T⁴⁵ | |
| 279 | N | NH | | H | CH₃CH₂ | Cl | | T⁴⁶ | |
| 280 | N | NH | | H | CH₃CH₂ | Cl | | T⁴⁷ | |
| 281 | N | NH | | H | CH₃CH₂ | Cl | | T⁴⁹ | |
| 282 | N | NH | | H | CH₃CH₂ | Cl | | T⁵⁰ | |
| 283 | N | NH | | H | CH₃CH₂ | Cl | | T⁵¹ | |
| 284 | N | NH | | H | CH₃CH₂ | Cl | | T⁵³ | |
| 285 | N | NH | | H | CH₃CH₂ | Cl | | T⁵⁴ | |
| 286 | N | NH | | H | CH₃CH₂ | Cl | | T⁵⁵ | |
| 287 | N | NH | | H | CH₃CH₂ | Cl | | T⁵⁶ | |
| 288 | N | NH | | H | CH₃CH₂ | Cl | | T⁵⁷ | |
| 289 | N | NH | | H | CH₃CH₂ | Cl | | T⁵⁸ | |
| 290 | N | NH | | H | CH₃CH₂ | Cl | | T⁵⁹ | |
| 291 | N | NH | | H | CH₃CH₂ | Cl | | T⁶⁰ | |
| 292 | N | NH | | H | CH₃CH₂ | Cl | | T⁶³ | |
| 293 | N | NH | | H | CH₃CH₂ | Cl | | T⁶⁴ | |
| 294 | N | NH | | H | CH₃CH₂ | Cl | | T⁶⁶ | |
| 295 | N | NH | | H | CH₃CH₂ | Cl | | T⁶⁷ | |
| 296 | N | NH | | H | CH₃CH₂ | Cl | | T⁶⁸ | |
| 297 | N | NH | | H | CH₃CH₂ | Cl | | T⁷⁰ | |
| 298 | N | NH | | H | CH₃CH₂ | Cl | | T⁷¹ | |
| 299 | N | NH | | H | CH₃CH₂ | Cl | | T⁷² | |
| 300 | N | NH | | H | CH₃CH₂ | Cl | | T⁷⁴ | |
| 301 | N | NH | | H | CH₃CH₂ | Cl | | T⁷⁵ | |
| 302 | N | NH | | H | CH₃CH₂ | Cl | | T⁷⁷ | |
| 303 | N | NH | | H | CH₃CH₂ | Cl | | T⁷⁸ | |
| 304 | N | NH | | H | CH₃CH₂ | Cl | | T⁸⁰ | |
| 305 | N | NH | | H | CH₃CH₂ | Cl | | T⁸³ | |
| 306 | N | NH | | H | CH₃CH₂ | Cl | | T⁸⁵ | |
| 307 | N | NH | | H | CH₃CH₂ | Cl | | T⁸⁶ | |
| 308 | N | NH | | H | CH₃CH₂ | Cl | | T⁸⁷ | |
| 309 | N | NH | | H | CH₃CH₂ | Cl | | T⁸⁸ | |
| 310 | N | NH | | H | CH₃CH₂ | Cl | | T⁹⁰ | |
| 311 | N | NH | | H | CH₃CH₂ | Cl | | T⁹² | |
| 311a | N | NH | | H | CH₃CH₂ | Cl | | T⁹³ | |
| 312 | N | NH | | H | CH₃CH₂ | Cl | | T⁹⁵ | |
| 313 | N | NH | | H | CH₃CH₂ | Cl | | T⁹⁶ | |
| 314 | N | NH | | H | CH₃CH₂ | Cl | | T⁹⁷ | |
| 315 | N | NH | | H | CH₃CH₂ | Cl | | T⁹⁸ | |
| 316 | N | NH | | H | CH₃CH₂ | Cl | | T⁹⁹ | |

TABLE 4-continued

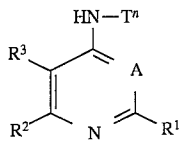

| Example No. | A | B | D | E | G | X | R¹ | Tⁿ | m.p. [°C.] |
|---|---|---|---|---|---|---|---|---|---|
| 317 | N | NH | | H | CH₃CH₂ | Cl | | T¹⁰¹ | |
| 318 | N | NH | | H | CH₃CH₂ | Cl | | T¹⁰² | |
| 319 | N | NH | | H | CH₃CH₂ | Cl | | T¹⁰³ | |
| 320 | N | NH | | H | CH₃CH₂ | Cl | | T¹⁰⁴ | |
| 321 | N | NH | | H | CH₃CH₂ | Cl | | T¹⁰⁵ | |
| 322 | N | NH | | H | CH₃CH₂ | Cl | | T¹⁰⁶ | |
| 323 | N | NH | | H | CH₃CH₂ | Cl | | T¹⁰⁷ | |
| 324 | N | NH | | H | CH₃CH₂ | Cl | | T¹⁰⁸ | |
| 325 | N | NH | | H | CH₃CH₂ | Cl | | T¹⁰⁹ | |
| 326 | N | NH | | H | CH₃CH₂ | Cl | | T¹¹⁰ | |
| 327 | N | NH | | H | CH₃CH₂ | Cl | | T¹¹¹ | |
| 328 | N | NH | | H | CH₃CH₂ | Cl | | T¹¹² | |
| 329 | N | NH | | H | CH₃CH₂ | Cl | | T¹¹³ | |
| 330 | N | NH | | H | CH₃CH₂ | Cl | | T¹¹⁴ | |
| 331 | N | NH | | H | CH₃CH₂ | Cl | | T¹¹⁵ | |
| 332 | N | NH | | H | CH₃CH₂ | Cl | | T¹¹⁶ | |

TABLE 5

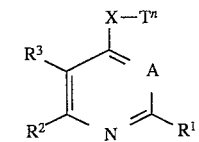

| Example No. | A | B | D | E | G | X | R¹ | Tⁿ | m.p. [°C.] |
|---|---|---|---|---|---|---|---|---|---|
| 333 | N | NH | | H | | CH₃ | Cl | T⁶ | |
| 334 | N | NH | | H | | CH₃ | Cl | T⁶ | |
| 335 | N | NH | | H | | CH₃ | Br | T⁶ | |
| 336 | N | NH | | H | | CF₃ | Cl | T⁶ | |
| 337 | N | NH | | H | | CH₂CH₃ | Cl | T⁶ | |
| 338 | N | NH | | H | | CH₂CH₃ | Br | T⁶ | |
| 339 | N | NH | | H | | CH₃CHF | Cl | T⁶ | |
| 340 | N | NH | | H | | CH₃CHCl | CL | T⁶ | |
| 341 | N | NH | | H | | CF₃CH₂ | Cl | T⁶ | |
| 342 | N | NH | | H | | CF₃CH₂ | Cl | T⁶ | |
| 343 | N | NH | | H | | CF₂HCF₂ | Cl | T⁶ | |
| 344 | N | NH | | H | | CH₃CH₂CH₂ | Cl | T⁶ | |
| 345 | N | NH | | H | | CH₃CH₂CH₂ | Br | T⁶ | |
| 346 | N | NH | | H | | CH₃CH(CH₃) | Cl | T⁶ | |
| 347 | N | NH | | H | | CH₃CH(CH₃) | Br | T⁶ | |
| 348 | N | NH | | H | | CH₃(CH₂)₃ | Cl | T⁶ | |
| 349 | N | NH | | H | | CH₃ | CH₃O | T⁶ | |
| 350 | N | NH | | H | | CF₃ | CH₃O | T⁶ | |
| 351 | N | NH | | H | | CH₃CH₂ | CH₃O | T⁶ | |
| 352 | N | O | | H | | CH₃ | Cl | T⁶ | |
| 353 | N | O | | H | | CH₃ | Br | T⁶ | |
| 354 | N | O | | H | | CF₃ | Cl | T⁶ | |
| 355 | N | O | | H | | CH₂CH₃ | Cl | T⁶ | |
| 356 | N | O | | H | | CH₂CH₃ | Br | T⁶ | |
| 357 | N | O | | H | | CH₃CHF | Cl | T⁶ | |
| 358 | N | O | | H | | CH₃CHCl | CL | T⁶ | |
| 359 | N | O | | H | | CF₃CH₂ | Cl | T⁶ | |
| 360 | N | O | | H | | CF₂HCF₂ | Cl | T⁶ | |
| 361 | N | O | | H | | CH₃CH₂CH₂ | Cl | T⁶ | |
| 362 | N | O | | H | | CH₃CH₂CH₂ | Br | T⁶ | |
| 363 | N | O | | H | | CH₃CH(CH₃) | Cl | T⁶ | |
| 364 | N | O | | H | | CH₃CH(CH₃) | Br | T⁶ | |
| 365 | N | O | | H | | CH₃(CH₂)₃ | Cl | T⁶ | |
| 366 | N | O | | H | | CH₃ | CH₃O | T⁶ | |
| 367 | N | O | | H | | CF₃ | CH₃O | T⁶ | |
| 368 | N | O | | H | | CH₃CH₂ | CH₃O | T⁶ | |
| 369 | N | O | | H | | CF₂HCF₂ | CH₃O | T⁶ | |
| 370 | N | O | | H | | CH₃OCH₂ | CH₃O | T⁶ | |
| 371 | N | S | | H | | CH₃CH₂ | Cl | T⁶ | |

TABLE 5-continued

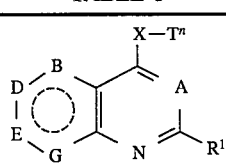

| Example No. | A | B | D | E | G | X | R¹ | Tⁿ | m.p. [°C.] |
|---|---|---|---|---|---|---|---|---|---|
| 372 | N | SO | H | | | $CH_3CH_2$ | Cl | $T^6$ | |
| 373 | N | $SO_2$ | H | | | $CH_3CH_2$ | Cl | $T^6$ | |

TABLE 6

| Example No. | A | B | D | E | G | X | R¹ | Tⁿ | m.p. [°C.] |
|---|---|---|---|---|---|---|---|---|---|
| 374 | N | $CH_2$ | $CH_2$ | $CH_2$ | — | NH | H | $T^6$ | |
| 375 | N | $CH_2$ | $CH_2$ | $CH_2$ | $CH_2$ | NH | H | $T^6$ | |
| 376 | N | $CH_2$ | $CH_2$ | $CH_2$ | $CH_2CH_2$ | NH | H | $T^6$ | |
| 377 | N | O | $CH_2$ | $CH_2$ | $CH_2$ | NH | H | $T^6$ | |
| 378 | N | $CH_2$ | O | $CH_2$ | $CH_2$ | NH | H | $T^6$ | |
| 379 | N | O | $CH_2$ | O | $CH_2$ | NH | H | $T^6$ | |
| 380 | N | S | $CH_2$ | $CH_2$ | $CH_2$ | NH | H | $T^6$ | |
| 381 | N | $CH_2$ | S | $CH_2$ | $CH_2$ | NH | H | $T^6$ | |
| 382 | CH | CH | CH | CH | CH | NH | H | $T^6$ | |
| 383 | CH | CH | CH | CH | CF | NH | H | $T^6$ | |
| 384 | N | CH | CH | CH | CH | NH | H | $T^6$ | |
| 385 | N | CF | CH | CH | CH | NH | H | $T^6$ | |
| 386 | N | CH | CH | CH | N | NH | H | $T^6$ | |
| 387 | N | $CCH_3$ | CH | CH | CH | NH | H | $T^6$ | |
| 388 | N | CH | CF | CH | CH | NH | H | $T^6$ | |
| 389 | N | $CH_2$ | $CH_2$ | $CH_2$ | — | O | H | $T^6$ | |
| 390 | N | $CH_2$ | $CH_2$ | $CH_2$ | $CH_2$ | O | H | $T^6$ | |
| 391 | N | $CH_2$ | $CH_2$ | $CH_2$ | $CH_2CH_2$ | O | H | $T^6$ | |
| 392 | N | O | $CH_2$ | $CH_2$ | $CH_2$ | O | H | $T^6$ | |
| 393 | N | $CH_2$ | O | $CH_2$ | $CH_2$ | O | H | $T^6$ | |
| 394 | N | O | $CH_2$ | O | $CH_2$ | O | H | $T^6$ | |
| 395 | N | S | $CH_2$ | $CH_2$ | $CH_2$ | O | H | $T^6$ | |
| 396 | N | $CH_2$ | S | $CH_2$ | $CH_2$ | O | H | $T^6$ | |
| 397 | N | $CH_2$ | $CH_2$ | $CH_2$ | $CH_2$ | S | H | $T^6$ | |
| 398 | CH | CH | CH | CH | CH | O | H | $T^6$ | |
| 399 | CH | CH | CH | CH | CF | O | H | $T^6$ | |
| 400 | N | CH | CH | CH | CH | O | H | $T^6$ | |
| 401 | N | CF | CH | CH | CH | O | H | $T^6$ | |
| 402 | N | CH | CH | CH | N | O | H | $T^6$ | |
| 403 | N | $CCH_3$ | CH | CH | CH | O | H | $T^6$ | |
| 404 | N | CH | CF | CH | CH | O | H | $T^6$ | |
| 405 | N | CH | CH | CH | CH | S | H | $T^6$ | |

B. Formulation Examples a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium ligninsulfonate and 1 part by weight of sodium oleylmethyltaurinate as wetting and dispersing agent, and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium ligninsulfonate and 51 parts by weight of water, and grinding the mixture in a bowl mill to a fineness of below 5 microns.

d) An emulsifiable concentrate can be prepared from 15 parts by weight of active substance, 75 parts by weight of cyclohexane as solvent and 10 parts by weight of ethyoxlated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, followed by drying and intimate mixing. The wettable powder amounts to approximately 5% by weight and the inert carrier material to approximately 95% of the finished granules.

C. Biological Examples

Example 1: *Erysiphe graminis*

Barley plants in the 3-leaf stage were heavily inoculated with conidia of powdery mildew of barley (*Erysiphye graminis* f. sp. hordei) and placed in a greenhouse at 20° C. at a relative atmospheric humidity of 90–95%. 24 hours after inoculation, the plants were wetted uniformly with the compounds listed below at the active substance concentrations given. After an incubation period of 10 days, the plants were examined for attack by powdery mildew of barley. The severity of the disease was expressed in % of diseased leaf area in comparison with untreated contol plants with a disease incidence of 100%.

The substances of the following examples from the tables suppress the disease completely at 250 mg of active substance/l of spray mixture: 197, 193, 205, 225, 201, 99 and 103.

Example 2: *Leptosphaeria nodorum*

Wheat plants of the variety "Jubilar" in the 2-leaf stage were treated to run-off point with aqueous suspensions of the claimed compounds. After the spray coating had dried, the plants were inoculated with an aqueous pyknospore suspension of Leptosphaeria nodorum and incubated for several hours in a controlled environment cabinet at a relative atmospheric humidity of 100%. The plants were grown on in the greenhouse at a relative atmospheric humidity of approximately 90% until the symptoms became visible.

Approximately one week after the inoculation, the disease level was scored in % of the leaf area in comparison with untreated control plants with a disease incidence of 100%.

The substances of the following examples from the tables suppress the disease completely at 250 mg of active substance/l of spray mixture: 193 and 201.

Example 3

Bean plants (Phaseolus v.) which were heavily populated with the 2-spotted spider mite (*Tetranychus urticae*, full population) were sprayed with an aqueous dilution of a wettable powder concentrate containing 250 ppm of the active substance in question.

The mortality of the mites was checked after 7 days. A destruction of 100% was achieved with the compounds of Examples 193, 197, 201, 205, 225, 217, 221, 103 and 99 in the tables.

Example 4

Field beans (*Vicia faba*) which were densely populated with the black bean aphid (*Aphis fabae*) were sprayed with aqueous dilutions of wettable powder concentrates with an active substance content of 250 ppm until the stage of commencement of run-off was reached. The mortality of the aphids is determined after 3 days. A destruction of 100% can be achieved with the compounds of Examples 193, 197, 103, 99, 71 and 35 in the tables.

Example 5

Bean plants which were densely populated with whitefly (*Trialeurodes vaporariorum*) were sprayed with aqueous suspensions of wettable powder concentrates (active substance content 250 ppm) until the stage of commencement of run-off was reached. After the plants were placed in the greenhouse, they were checked under the microscope after 14 days, the result being in each case 100% mortality in the case of the preparations with active substances of Examples 193, 197, 201, 225, 217 and 221 of the tables.

Example 6

The bottom and the lid of a Petri dish are coated on the inside with in each case 3 ml of an aqueous dilution of a wettable powder concentrate containing 250 ppm of the active substance in question. After the coating had dried, 24-hour old houseflies (*Musca domestica*) were introduced into the Petri dishes, and the latter were sealed with the treated lids. After 3 hours at room temperature (20° C.), the mortality of the flies was checked. A destruction of 100% was achieved with the compounds of Examples 193, 197 and 221 of the tables.

Example 7

Filter paper disks were treated with in each case 1 ml of the aqueous dilution of a wettable powder concentrate containing 250 ppm of the active substance in question and stored in the open until they had dried. Then, the filter paper was placed on the bottom of a Petri dish and in each case 1 ml of (distilled water) was added. 10 larvae (L3) of *Diabrotica undecimpunctata* were subsequently placed on the filter paper, and the Petri dish was sealed and stored for 48 hours at 28° C. in the dark. The mortality of the larvae was then determined. A destruction of 100% was achieved with the compound of Example 193 of the tables.

Example 8

Rice seed was germinated under moist conditions and grown in dishes until approximately 10 cm high. Batches of 3 rice plants were planted in glass tubes into which wet cotton wadding had been introduced, and the leaves of the rice plants were immersed in an aqueous dilution of a wettable powder concentrate containing 250 ppm of the active substance in question. After the coating had dried, the plants together with the tube were placed on the bottom of a dish, batches of 10 specimens of the brown planthopper (*Nilaparvata lugens*, L3) were introduced into the dish, and the dish was sealed and kept at 25° C. The mortality of the planthoppers was checked after 3 days. A destruction of 100% was achieved with the compound of Example 197 of the tables.

Example 9

Active substances were dissolved in methanol, and the solutions were injected into larvae (L4) of the cockroach, *Blaberus craniifer*.

A 100% mortality was found 48 hours after application of the compounds of Examples 17, 19 and 217 of the tables. ($2 \times 10^{-4}$ g of a.i./animal).

We claim:

1. A compound of the formula I

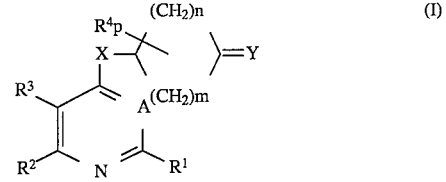

or acid addition salt thereof, in which

A is N $R^1$ is hydrogen, halogen, $(C_1-C_4)$-alkyl or $(C_3-C_6)$-cycloalkyl, $R^2$ is hydrogen, halogen, $(C_1-C_4)$-alkyl or $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-haloalkyl, $(C_1-C_4)$-alkylthio, $(C_1-C_4)$-alkylthio-$(C_1-C_4)$-alkyl, $(C_1-C_4)$-alkylamino or di-$(C_1-C_4)$-alkylamino, $R^3$ is hydrogen, halogen, $(C_1-C_4)$-alkyl or $(C_1-C_4)$-haloalkyl, $(C_1-C_4)$-alkoxy, $(C_1-C_4)$ haloalkoxy, $(C_1-C_4)$-alkylthio, amino, $(C_1-C_4)$-alkylamino or di- $(C_1-C_4)$ alkylamino, or $R^2$ and $R^3$ together with the carbon atoms to which they are bonded form an unsaturated 5- or 6-membered carbocyclic ring in which one or two CH groups are optionally replaced by nitrogen atoms and in which, in the event that it is a 5-membered ring, one $CH_2$ group is optionally replaced by an oxygen or sulfur atom and which is optionally substituted by 1, 2 or 3 identical or different radicals, these radicals being (Cl-C4)-alkyl or $(C_1-C_4)$-alkoxy, $(C_1-C_4)$-haloalkyl, $(C_1-C_4)$-haloalkoxy and/or halogen, or $R^2$ and $R^3$ together with the carbon atoms to which they are bonded form a saturated 5-, 6- or 7-membered carbocyclic ring in which one or two $CH_2$ groups are optionally replaced by oxygen or sulfur atoms and which is optionally substituted by one to four identical or different radicals selected from the group consisting of $(C_1-C_4)$alkyl and halogen, X is oxygen, NH and $S(O)_q$, wherein q is 0, 1 or 2, $R^4$ is halogen, $(C_1-C_4)$-alkyl, $(C_3-C_7)$-cycloalkyl, $(C_1-C_4)$haloalkyl, $(C_1-C_4)$-alkoxy, $(C_1-C_4)$-haloalkoxy or optionally substituted phenyl, p is an integer from 0 to 4, n is an integer from 0 to 2 and m is an integer from 1 to 3, y is

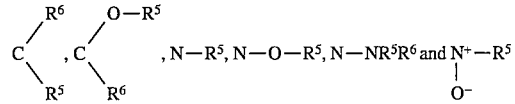

$R^5$ is hydrogen, halogen, $(C_1-C_{12})$-alkyl, $(C_3-C_8)$-cycloalkyl, $(C_3-C_8)$ -cycloalkyl-$(C_1-C_4)$ -alkyl, $_t$-$(C_1-C_4)$-alkyl, wherein t is an integer from 1 to 3, $(C_1-C_{12})$-haloalkyl, 2-(tetra-hydro-2H-pyran-2-yloxy)-$(C_1-C_4)$-alkyl, $_t$-$(C_1-C_4)$-haloalkyl, $(C_1-C_4)$ -alkenyl, $(C_1-C_8)$-alkylcarbonyl, $(C_1-C_8$-alkoxycarboxyl, $(C_1-C_8)$ -alkylcarbonyl-($C_1$–$C_4$)-alkyl, ($C_1$–$C_8$)-haloalkylcarbonyl, ($C_1$–$C_8$)-haloalkoxycarbonyl, ($C_3$–$C_8$)-cycloalkylcarbonyl, ($C_3$–$C_8$) -cycloalkoxycarbonyl, ($C_3$–$C_8$)-optionally substituted benzoyl, the term "optionally substituted benzoyl" meaning a radical in which the phenyl moiety is substituted as in "optionally substituted phenyl"; and the term "optionally substituted phenyl" meaning a phenyl radical which has one, two or three identical or different substituents selected from the series consisting of halogen, ($C_1$–$C_4$)-alkyl, ($C_1$–$C_4$)-alkoxy, ($C_1$–$C_4$)-haloalkyl, and ($C_1$–$C_4$)-haloalkoxy; benzyloxycarbonyl, ($C_2$–$C_8$)-alkenyl, ($C_3$–$C_8$)-alkynyl, tri-($C_3$–$C_8$)-alkylsilyl, di-($C_1$–$C_8$)-alkyl-($C_3$–$C_8$)-cycloalkylsilyl, di-($C_1$–$C_8$)-alkyl-(phenyl-($C_1$ –$C_4$)-alkyl)-silyl, di($C_1$–$C_8$)-alkyl-($C_1$–$C_4$)-haloalkylsilyl, dimethylphenylsilyl, heteroaryl selected from the group consisting of thienyl, benzothienyl, furyl, benzofuryl, pyrrolyl, imidazolyl, pyrazolyl, pyridyl, pyrazinyl, pyrimidinyl, pyridazinyl, indolizinyl, isoindolyl, indolyl, indazolyl, purinyl, quinolyl, isoquinolyl, phthalazinyl, naphthydrinyl, quinoxalinyl, quinazolinyl, cinnolinyl, pteridinyl, oxazolyl, isoxazolyl, thiazolyl, isothiazolyl, tetrazolyl; phenyl, phenyl-($C_2$–$C_4$)-alkyl, benzyl, benzyloxy-($C_1$–$C_4$)-alkyl, it being possible for phenyl or heteroaryl in the last-mentioned six radicals to be unsubstituted or mono- or polysubstituted, and these substituents, which are identical or different, are in each case halogen, ($C_1$–$C_4$)-alkyl, ($C_3$–$C_8$)-cycloalkyl, ($C_1$–$C_4$)-haloalkyl, ($C_1$–$C_4$)-dialkylamino, ($C_1$–$C_4$)-alkylthio, ($C_1$–$C_8$)-alkoxy, ($C_1$–$C_8$)-alkoxycarbonyl, ($C_1$–$C_8$)-alkanoyloxy, ($C_1$–$C_4$)-haloalkoxy, ($C_1$–$C_4$)-alkoxy-($C_1$–$C_4$)-alkoxy, $_r$-($C_2$–$C_4$)-alkyl, 2-(tetrahydro-2H-pyran-2-yloxy)-ethoxy, ($C_2$–$C_8$) alkenyl, ($C_2$–$C_8$)-alkynyl, phenoxy or benzyloxy which has optionally one more, identical or different substituents selected from the group consisting of ($C_1$–$C_4$)-alkyl or ($C_1$–$C_4$)-haloalkyl, ($C_1$–$C_4$)-alkoxy, ($C_1$–$C_4$)-haloalkoxy and halogen in the phenyl radical, $R^6$ is hydrogen, halogen, ($C_1$–$C_8$)-alkyl, ($C_3$–$C_8$)-cycloalkyl, ($C_1$–$C_8$) haloalkyl, phenyl and benzyl, wherein the phenyl rings are optionally substituted as described above under $R^5$, or $R^5$ and $R^6$ together can form a 3- to 7-membered ring which can optionally be substituted by one, two or three identical or different radicals selected from the group consisting of halogen, ($C_1$–$C_4$)-alkyl, ($C_1$–$C_4$)-alkoxy, ($C_1$–$C_4$)-haloalkyl, ($C_1$–$C_4$)-haloalkyl and ($C_1$–$C_4$)-haloalkoxy and in which one $CH_2$ group is optionally replaced by O, S, $NR^7$ wherein $R^7$ is as defined for $R^4$ but must not be halogen.

2. A compound of the formula I as claimed in claim 1 or salt thereof, in which

A is as defined in claim 1, $R^1$ is hydrogen or methyl, $R^2$ is halogen, ($C_1$–$C_4$)-alkyl, ($C_1$–$C_4$)-haloalkyl, ($C_1$–$C_4$)-alkoxy or ($C_1$–$C_4$)-alkoxy-($C_1$–$C_4$)-alkyl, $R^3$ is hydrogen, halogen, ($C_1$–$C_3$)-alkyl, methoxy or ethoxy, or $R^2$ and $R^3$ together with the carbon atoms to which they are bonded form an unsaturated 5- or 6-membered ring which optionally contains one to two nitrogen atoms, an oxygen atom or a sulfur atom, or $R^2$ and $R^3$ together with the carbon atoms to which they are bonded form an unsaturated 5- or 6-membered ring which optionally contains a sulfur atom or 1 to 2 oxygen atoms, and $R^4$, $R^5$, $R^6$ and $R^7$ and X, Y, m, n, p are as defined in claim 1.

3. A compound of the formula I as claimed in claim 1 or salt thereof, in which

A is as defined in claim 1, $R^1$ is hydrogen $R^2$ is ($C_1$–$C_4$)-alkyl or methoxymethyl, $R^3$ is methyl, ethyl, methoxy, chlorine or bromine, or $R^2$ and $R^2$ together with the carbon atoms to which they are bonded form the quinoline or quinazoline system which is optionally substituted by fluorine, chloride, bromine or methyl, or $R^2$ and $R^3$ together with the carbon atoms to which they are bonded form an unsaturated 6-membered ring which contains a nitrogen atom, or $R^2$ and $R^3$ together with the carbon atoms to which they are bonded form a saturated 6-membered ring which optionally contains one or two oxygen atoms, m, n, p and X are as defined in claim 1, Y is

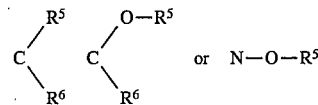

and $R^5$, and $R^6$ and $R^7$ are also as defined in claim 1.

4. A compound of the formula I as claimed in claim 1 or salt thereof, in which

A and $R^1$ to $R^7$ are as defined in claim 1 and m and n are 2, p is O, and

X is NH or an oxygen atom.

5. A compound of the formula I as claimed in claim 1 or salt thereof, in which

A is as defined in claim 1, $R^1$ is hydrogen, $R^2$ is ($C_1$–$C_4$)-alkyl or methoxymethyl, $R^3$ is chlorine, bromine or methoxy, or $R^2$ and $R^3$ together with the carbon atoms to which they are bonded form the quinoline or quinazoline system which is optionally substituted by fluorine, chlorine, bromine or methyl, or $R^2$ and $R^3$ together with the pyrimidine ring form the 5, 6, 7, 8-tetrahydroquinazoline system or the 5, 6, dihydro-7H-pyranopyramidine system, m and n are the number two and p is zero, X is NH or an oxygen atom, Y is

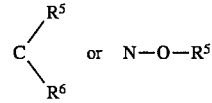

$R^5$, $R^6$ and $R^7$ are as defined in claim 1.

6. A compound of the formula as claimed in claim 1 or salt thereof, in which

A is as defined in claim 1, $R^1$ is hydrogen, $R^2$ is methoxymethyl and $R^3$ is methoxy, or $R^2$ is ($C_1$–$C_4$)-alkyl and $R^3$ is chlorine or bromine, or $R^2$ and $R^3$ together with the carbon atom to which they are bonded form a quinoline or quinazoline system which is substituted by fluorine, chlorine or methyl, or a 5, 6, 7, 8-tetrahydroquinazoline system or the 5,6-dihydro-7H-pyranopyrimidine system, m, n, p, X and Y are as defined in claim 1.

$R^5$ is $(C_1-C_4)$-alkyl, cyclopentyl, cyclohexyl, $(C_1-C_8)$-alkylcarbonyl, $(C_1-C_8)$-alkoxycarbonyl, phenyl, benzyl or benzoyl, it being possible for the last-mentioned three radicals to be unsubstituted or to be provided with one or two substituents which can be identical or different and are fluorine, chlorine, bromine, $(C_1-C_4)$-alkyl, $(C_1-C_4)$-alkoxy, trifluromethyl, $(C_1-C_2)$-haloalkoxy, cyclohexyl, 2-ethoxyethoxy, methylthio or dimethylamino, and $R^6$ and $R^7$ are as defined in claim 1.

7. An insecticidal, acaricidal, or nematicidal composition comprising an effective amount of one or more compounds as claimed in claim 1 and an inert carrier.

8. A method of controlling harmful insects, Acarina and nematodes, in which an effective amount of a compound as claimed in claim 1 is applied to these harmful insects, Acarina and nematodes or to the plants, areas, or substrates attacked by them.

* * * * *